US005958671A

United States Patent [19]
Glimcher et al.

[11] Patent Number: 5,958,671
[45] Date of Patent: Sep. 28, 1999

[54] METHODS AND COMPOSITIONS FOR REGULATING T CELL SUBSETS BY MODULATING TRANSCRIPTION FACTOR ACTIVITY

[75] Inventors: Laurie H. Glimcher, West Newton; I-Cheng Ho, Newton, both of Mass.

[73] Assignee: Presidents and Fellows of Harvard College, Cambridge, Mass.

[21] Appl. No.: 08/636,602

[22] Filed: Apr. 23, 1996

[51] Int. Cl.[6] .............................. C12Q 1/02; C12Q 1/68; C12N 5/06; C12N 15/09
[52] U.S. Cl. ................................. 435/4; 435/6; 435/29; 435/375; 435/455
[58] Field of Search .......................... 435/4, 29, 6, 172.3, 435/375, 34–37, 455

[56] References Cited

FOREIGN PATENT DOCUMENTS

| 585 681 A2 | 3/1994 | European Pat. Off. |
| WO 95/24425 | 9/1995 | WIPO |
| WO 95/27500 | 10/1995 | WIPO |

OTHER PUBLICATIONS

Andrews, N.C. et al., "The ubiquitous subunit of erythroid transcription factor NF–E2 is a small basic–leucine Zipper protein related to the v–maf oncogene", *Proc. Natl. Acad. Sci. USA*, vol. 90, pp. 11488–11492 (1993).

Casolaro, V., et al., "Inhibition of NF–AT–dependent transcription by NF –kappa B: implications for differential gene expression in T helper cell subsets", *Proc Natl Acad Sci USA*, vol. 92, pp. 11623–11627 (1995).

Cordes, S.P. et al., "The mouse segmentation gene kr encodes a novel basic domain–leucine zipper transcription factor", *Cell*, pp. 1025–1034 (1994).

Engel, J.D., "Meticulous AP–1 factors", *Nature*, vol. 367, pp. 516–517 (1994).

Hodge, M.R. et al., "The proximal promoter of the IL–4 gene is composed of multiple essential regulatory sites that bind at least two distinct factors", *Journal of Immunology* vol. 154, No. 12, pp. 6397–6405 (1995).

Hodge, M.R. et al., "Hyperproliferation and dysregulation of IL–4 expression in NF–ATp–deficient mice", *Immunity* vol. 4, pp. 397–405 (1996).

Fujiwara, K.T. et al., "Two new members of the maf oncogene family, mafK and mafF, encode nuclear b–Zip proteins lacking putative trans–activator domain", *Oncogene*, vol. 8, pp. 2371–2380 (1993).

Igarashi, K. et al., "Conditional expression of the ubiquitous transcription factor MafK induces erytholeukemia cell differentiation", *Proc. Natl. Acad. Sci. USA*, vol. 92, pp. 7445–7449 (1995).

Igarashi, K. et al., "Activity and expression of murine small Maf family protein MafK", *J. Biol. Chem.*, vol. 270, pp. 7615–7624 (1995).

Itoh, K. et al., "Cloning and characterization of a novel erythroid cell–derived CNC family transcription factor heterodimerizing with the small Maf family proteins", *Mol. Cell. Biol.*, vol. 15:8, pp. 4184–4193 (1995).

Kataoka, K. et al., "Transactiviation activity of Maf nuclear oncoprotein is modulated by Jun, Fos and small Maf proteins", *Oncogene*, vol. 12, pp. 53–62 (1996).

Kataoka, K. et al., "Maf nuclear oncoprotein recognizes sequences related to an AP–1 site and forms heterodimers with both Fos and Jun", *Mol. Cell. Biol.*, vol. 14:1, pp. 700–712 (1994).

Kataoka, K. et al., "Structure–Function Analysis of the maf Oncogen Product, a Member of the b–Zip Protein Family", *J. Virol.*, vol. 67:4, pp. 2133–2141, (1993).

Kawai, S. et al., "Isolation of the avian transforming retrovirus, AS42, carrying the v–maf oncogene and initial characterization of its gene product", *Virology*, vol. 88, pp. 778–784 (1992).

Liu, Q. et al., "Expression of the bZIP Transcription factor gene Nrl in the developing nervous system", *Oncogene*, vol. 12, pp. 207–211 (1996).

Nishizawa M. et al., "v–maf, a viral oncogene that encodes a "leucine zipper" motif", *Proc. Natl. Acad. Sci. USA*, vol. 86, pp. 7711–7715 (1989).

Rooney, J.W. et al., "A common factor regulates both Th1–and Th2 –specific cytokine gene expression", *EMBO Journal*, vol. 13(3), pp. 625–633 (1994).

Rooney, J.W. et al., "Coordinate and cooperative roles for NF –AT and AP–1 in the regulation of the murine IL—4 gene", *Immunity*, vol. 2, pp. 473–483 (1995).

Sieweke, M.H. et al., "MafB is an interaction partner and repressor of Ets–1 that inhibits erythroid differentiation", *Cell*, vol. 85, pp. 49–60 (1996).

Swaroop, A. et al. "A conserved retina–specific gene encodes a basic motif/leucine zipper domain", *Proc. Natl. Acad. Sci. USA*, vol. 89, pp. 266–270 (1992).

Tara, D. et al., "Characterization of the constitutive and inducible components of a T cell IL—4 activation responsive element", *J Immunol*, vol. 154(9), pp. 4592–602 (1995).

(List continued on next page.)

*Primary Examiner*—Bruce R. Campell
*Assistant Examiner*—Scott D. Priebe
*Attorney, Agent, or Firm*—Lahive & Cockfield, LLP; Giulio A. DeConti, Jr.; Catherine J. Kara

[57] ABSTRACT

Methods for modulating production of a T helper type 2 (Th2)-associated cytokine, in particular interleukin-4, by modulating the activity of a transcription factor, in particular the proto-oncoprotein c-Maf, that regulates expression of the Th2-associated cytokine gene are disclosed. Methods for modulating development of T helper type 1 (Th1) or T helper type 2 (Th2) subsets in a subject using agents that modulate transcription factor activity are also disclosed. The methods of the invention can further involve use of agents that modulate the activity of additional transcription factors that contribute to the regulation of Th1- or Th2-associated cytokines, such as a Nuclear Factor of Activated T cells (NF-AT) protein and/or an AP-1 family protein. Compositions for modulating Th2-associated cytokine production, recombinant expression vectors and host cells, as well as screening assays to identify agents that modulate c-Maf activity, are also disclosed.

27 Claims, 12 Drawing Sheets

OTHER PUBLICATIONS

Wierenga, E.A. et al., Reduced NF –AT binding at the IL—4—CLEO. element in TH2 cells of atopic patients; *9th International Congress of Immunology*, Abstract 4155, Jul. 23–29 1995.

Yang–Feng, T.L. et al., "Neural retina–specific leucine zipper gene NRL (D14S46E) maps to human chromosome 14q11.1–q11.2", *Genomics*, vol. 14, pp. 491–492 (1992).

Kataoka et al. Small Maf proteins heterodimerize with Fos and may act as competitive repressors of the NF–E2 transcription factor. Molec. Cell. Biol. 15(4): 2180–2190, Mar. 2, 1995.

Kurschner et al. The maf proto–oncogen stimulates transcription from multiple sites in a promoter that directs Pukinje neuron–specific gene expression. Molec. Cell. Biol. 15(1): 246–254, Jan. 1995.

Peterson et al. "Transcription factor based therapeutics: drugs of the future", Trends in Biotech. 14: 11–18, Jan. 1993.

Kerppola et al. "Maf and Nrl can bind to AP–1 sites and form heterodimers with Fos and Jun", Oncogene 9: 675–684, Mar. 1994.

Igarishi et al. Regulation of transcription by dimerization of erythroid factor NF–E2 p45 with small Maf proteins. Nature 367: 568–572, Feb. 1994.

Ho et al. "The proto–oncogene c–maf is responsible for tissue–specific expression of interleukin–4", Cell 85: 973–983, Jun. 1996.

METHODS AND COMPOSITIONS FOR REGULATING T CELL SUBSETS BY MODULATING TRANSCRIPTION FACTOR ACTIVITY

GOVERNMENT FUNDING

Work described herein was supported, at least in part, under grant AI37833 awarded by the National Institutes of Health. The U.S. government therefore may have certain rights in this invention.

BACKGROUND OF THE INVENTION

CD4+ T helper cells are not a homogeneous population but can be divided on the basis of cytokine secretion into at least two subsets termed T helper type 1 (Th1) and T helper type 2 (Th2) (see e.g., Mosmann, T. R. et al. (1986) *J. Immunol.* 136:2348–2357; Paul, W. E. and Seder, R. A. (1994) *Cell* 76:241–251; Seder, R. A. and Paul, W. E. (1994) *Ann. Rev. Immunol.* 12:635–673). Th1 cells secrete interleukin-2 (IL-2) and interferon-γ (IFN-γ) while Th2 cells produce interleukin-4 (IL-4), interleukin-5 (IL-5), interleukin-10 (IL-10) and interleukin-13 (IL-13). Both subsets produce cytokines such as tumor necrosis factor (TNF) and granulocyte/macrophage-colony stimulating factor (GM-CSF). In addition to their different pattern of cytokine expression, Th1 and Th2 cells are thought to have differing functional activities. For example, Th1 cells are involved in inducing delayed type hypersensitivity responses, whereas Th2 cells are involved in providing efficient "help" to B lymphocytes and stimulating production of IgGI and IgE antibodies.

There is now abundant evidence that the ratio of Th1 to Th2 cells is highly relevant to the outcome of a wide array of immunologically-mediated clinical diseases including autoimmune, allergic and infectious diseases. For example, in experimental leishmania infections in mice, animals that are resistant to infection mount predominantly a Th1 response, whereas animals that are susceptible to progressive infection mount predominantly a Th2 response (Heinzel, F. P., et al. (1989) *J. Exp. Med.* 169:59–72; Locksley, R. M. and Scott, P. (1992) *Immunoparasitology Today* 1:A58–A61). In murine schistosomiasis, a Th1 to Th2 switch is observed coincident with the release of eggs into the tissues by female parasites and is associated with a worsening of the disease condition (Pearce, E. J., et al. (1991) *J. Exp. Med.* 173:159–166; Grzych, J-M., et al (1991) *J. Immunol.* 141:1322–1327; Kullberg, M. C., et al. (1992) *J. Immunol.* 148:3264–3270). Many human diseases, including chronic infections (such as with human immunodeficiency virus (HIV) and tuberculosis) and certain metastatic carcinomas, also are characterized by a Th1 to Th2 switch (see e.g., Shearer, G. M. and Clerici, M. (1992) *Prog. Chem. Immunol.* 54:21–43; Clerici, M and Shearer, G. M. (1993) *Immunology Today* 14:107–111; Yamarnura, M., et al. (1993) *J. Clin. Invest.* 91:1005–1010; Pisa, P., et al. (1992) *Proc. Natl. Acad. Sci. USA* 89:7708–7712; Fauci, A. S. (1988) *Science* 239:617–623). Furthermore, certain autoimmune diseases have been shown to be associated with a predominant Th1 response. For example, patients with rheumatoid arthritis have predominantly Th1 cells in synovial tissue (Simon, A. K., et al. (1994) *Proc. Natl. Acad. Sci. USA* 91:8562–8566) and experimental autoimmune encephalomyelitis (EAE) can be induced by autoreactive Th1 cells (Kuchroo, V. K., et al. (1993) *J. Immunol.* 151:4371–4381).

The ability to alter or manipulate ratios of Th1 and Th2 subsets requires an understanding of the mechanisms by which the differentiation of CD4 T helper precursor cells (Thp), which secrete only IL-2, choose to become Th1 or Th2 effector cells. It is clear that the cytokines themselves are potent Th cell inducers and form an autoregulatory loop (see e.g., Paul, W. E. and Seder, R. A. (1994) *Cell* 76:241–251; Seder, R. A. and Paul, W. E. (1994) *Ann. Rev. Immunol.* 12:635–673). Thus, IL-4 promotes the differentiation of Th2 cells while preventing the differentiation of precursors into Th1 cells, while IL-12 and IFN-γ have the opposite effect. One possible means therefore to alter Th1:Th2 ratios is to increase or decrease the level of selected cytokines. Direct administration of cytokines or antibodies to cytokines has been shown to have an effect on certain diseases mediated by either Th1 or Th2 cells. For example, administration of recombinant IL-4 or antibodies to IL-12 ameliorate EAE, a Th1-driven autoimmune disease (see Racke; M. K. et al. (1994) *J. Exp. Med.* 180:1961–1966; and Leonard, J. P. et al. (1995) *J. Exp. Med.* 181:381–386), while anti-IL-4 antibodies cure the Th2-mediated parasitic disease, *Leishmania major* (Sadick, M. D. et al. (1990) *J. Exp. Med.* 171:115–127). However, as therapeutic options, systemic administration of cytokines or antibodies may have unwanted side effects and, accordingly, alternative approaches to manipulating Th1/Th2 subsets are still needed.

The molecular basis for the tissue-specific expression of IL-4 in Th2 cells, or any T cell cytokine, has remained elusive. One possibility is the presence of repressor proteins that selectively silence cytokines. Transcriptional silencing has been well documented for bacteria, yeast and mammalian genes. Examples include *E. coli* thermoregulation genes (Goransson, M. et al. (1990) *Nature* 344:682–685), yeast α2 mating type genes (Keleher, C. A. et al. (1988) *Cell* 53:927–936) and mammalian MHC class I and TcRα genes (Weisman, J. D. and Singer, D. S. (1991) *Mol. Cell. Biol.* 11:4228–4234; Winoto, A. and Baltimore, D. (1989) *Cell* 59:649–655). Indeed, early experiments involving injection of IL-2 genomic DNA into Xenopus oocytes suggested the existence of a repressor protein for IL-2 in resting versus activated T cell extracts (Mouzaki, A. et al. (1991) *EMBO J.* 10:1399–1406). These studies suggested that the absence of IL-2 production in resting T cells was due to proteins that silenced the transcription of IL-2 by interacting with negative elements in the IL-2 promoter.

A second possibility is the existence of Th selective transactivators. A family of four related transcription factors called Nuclear Factor of Activated T cells (NF-AT), plays a key role in the regulation of cytokine gene expression (see e.g., Emmel, E. A. et al. (1989) *Science* 246:1617–1620; Flanagan, W. M. et al. (1991) *Nature* 352:803–807; Jain, J. et al. (1993) *Nature* 365:352–355; McCaffrey, P. G. et al. (1993) *Science* 262:750–754; Rao, A. (1994) *Immunol. Today* 15:274–281; Northrop, J. P. et al. (1994) *Nature* 369:497). However, NF-AT family members can bind to and transactivate the promoters of multiple cytokine genes including IL-2 and IL-4 (Rooney, J. et al. (1995) *Immunity* 2:545–553; Szabo, S. J. et al. (1993) *Mol. Cell. Biol.* 13:4793–4805; Flanagan, W. M. et al. (1991) *Nature* 352:803–807; Northrop, J. P. et al. (1994) *Nature* 369:497). Thus, they are not likely to be responsible for directing Th1- or Th2-specific cytokine transcription. Most, if not all, NF-AT binding sites in cytokine promoter regulatory regions are accompanied by nearby sites that bind auxiliary transcription factors, usually members of the AP-1 family. It has been shown that NF-AT and AP-1 proteins bind coordinately and cooperatively and are required for full activity of the IL-2 and IL-4 promoters. Different AP-1 proteins, specifically c-Jun, c-Fos, Fra-1, Fra-2, Jun B and Jun D, have been shown to bind to these sites (Rao, A. et al. (1994) *Immunol. Today* 15:274–281; Jain, J. et al. (1993) *Nature* 365:352–355; Boise, L. H. et al. (1993) *Mol. Cell. Biol.* 13:1911–1919; Rooney, J. et al. (1995) *Immunity* 2:545–553; Rooney, J. et al. (1995) *Mol. Cell. Biol.* 15:6299–6310). However, none of these AP-1 proteins is expressed in a Th1- or Th2-specific manner and there is no evidence for the differential recruitment of AP-1 family members to the IL-2 or IL-4 composite sites (Rooney, J. et al. (1995) *Mol. Cell. Biol.* 15:6299–6310). Thus, neither NF-AT proteins nor the AP-1 family members c-Jun, c-Fos, Fra-1, Fra-2, Jun B and Jun D can account for the tissue-specific transcription of IL-4 in Th2 cells.

SUMMARY OF THE INVENTION

This invention pertains to methods for regulating Th1 or Th2 subsets by modulating the activity of a transcription factor that regulates expression of a Th2-specific cytokine gene. As described further herein, it has now been discovered that the tissue-specific expression of IL-4 in Th2 cells is not due to a repressor protein but rather to a Th2-specific transactivator protein. The proto-oncogene c-mafhas now been demonstrated to be responsible for the tissue-specific expression of the Th2-associated cytokine interleukin-4. Moreover, ectopic expression of c-maf in cells other than Th2 cells (e.g, Th1 cells, B cells and non-lymphoid cells) leads to activation of the IL-4 promoter and, under appropriate conditions, production of endogenous IL-4.

Accordingly, in one aspect the invention provides a method for modulating production of a T helper type 2 (Th2)-associated cytokine by a cell. The method involves contacting the cell with an agent that modulates the activity of a transcription factor that regulates expression of a Th2-associated cytokine gene such that production of the Th2-associated cytokine by a cell is modulated. In particular, the agents of the invention act intracellularly to modulate the activity of a transcription factor that regulates expression of a Th2-associated cytokine gene. Preferably, the transcription factor is a member of the maf family. Most preferably, the transcription factor is c-Maf. The Th2-associated cytokine modulated in the method is preferably interleukin-4. In one embodiment, production of the Th2-associated cytokine (e.g., IL-4)is stimulated, for example in a cell that does not normally express the cytokine (such as a Th1 cell or a B cell). A variety of agents can be used to stimulate cytokine production, including a nucleic acid molecule encoding a maf family protein that is introduced into and expressed in the cell and chemical agents that enhance the expression or activity of an endogenous maf family protein in the cell. In another embodiment, production of a Th2-associated cytokine by a cell (e.g., a Th2 cell) is inhibited. A variety of agents can be used to inhibit cytokine production, including antisense nucleic acid molecules that are complementary to a maf family gene, intracellular antibodies that bind maf family proteins (e.g., in the cell nucleus), inhibitory forms of maf family proteins (e.g., dominant negative forms) and chemical agents that inhibit the expression or activity of an endogenous maf family protein in the cell. Cytokine production by the cell can be modulated in vitro or in vivo. In one embodiment, a cell is contacted with a modulating agent in vitro and then is administered to a subject to thereby regulate the development of Th1 and/or Th2 subsets in the subject.

In another aspect, the invention provides methods for regulating the development of Th1 or Th2 subsets in a subject. In addition to the embodiment discussed above wherein ex vivo modified cells are administered to the subject, in another embodiment, these methods involve direct administration to the subject of an agent that modulates the activity of a transcription factor (e.g., a maf family member) that regulates expression of a Th2-associated cytokine gene (e.g., IL-4)such that development of Th1 or Th2 cells in the subject is modulated.

The methods of the invention can further involve the use of additional agents that modulate the activity of additional transcription factors that contribute to regulating the expression of Th1- or Th2-associated cytokines. Preferred additional agents are those which modulate the activity of a Nuclear Factor of Activated T cells (NF-AT) protein. Thus, in one embodiment, a stimulatory method of the invention can involve the use of a first agent that stimulates the expression and/or activity of a maf protein and a second agent that stimulates the expression and/or activity of an NF-AT protein. Similarly, an inhibitory method of the invention can involve the use of a first agent that inhibits the expression and/or activity of a maf protein and a second agent that inhibits the expression and/or activity of an NF-AT protein. Alternatively or additionally, the modulatory methods of the invention can involve the use of additional agents that modulate the activity of an AP-1 family protein.

The modulatory methods of the invention can be used to manipulate Th1:Th2 ratios in a variety of clinical situations. For example, inhibition of Th2 formation may be useful in allergic diseases, malignancies and infectious diseases whereas enhancement of Th2 formation may be useful in autoimmune diseases and organ transplantation.

Another aspect of the invention pertains to compositions that are useful for modulating the production of a Th2-associated cytokine by a cell and/or for modulating the development of Th1 or Th2 subsets in a subject. In one embodiment, these compositions include recombinant expression vectors that encode a maf family protein, wherein the maf-encoding sequences are operatively linked to regulatory sequences that direct expression of the maf family protein in a specific cell type, such as lymphoid cells (e.g., T cells or B cells) or hematopoietic stem cells. In another embodiment, these compositions include host cells, such as host lymphoid cells (e.g., host T cells or host B cells) or host hematopoietic stem cells, into which a recombinant expression vector encoding a maf family protein has been introduced.

Yet another aspect of the invention pertains to screening assays for identifying compounds that modulate the activity of a transcription factor that regulates expression of a Th2-associated cytokine gene. In one type of screening assay, an indicator cell which contains both 1) a recombinant expression vector encoding a transcription factor that regulates expression of a Th2-associated cytokine gene and 2) a vector comprising regulatory sequences of the Th2-associated cytokine gene operatively linked a reporter gene is used to identify compounds that modulate the expression and/or activity of the transcription factor. In another embodiment, a screening assay of the invention identifies proteins from Th2 cells that form a protein-protein interaction with a transcription factor (e.g., c-Maf) that regulates expression of a Th2-associated cytokine gene. In yet another embodiment, a screening assay of the invention identifies compounds that modulate the interaction of c-Maf with a maf response element (MARE) in the promoter of a Th2-associated cytokine gene (e.g., a MARE in the IL-4 promoter).

DETAILED DESCRIPTION OF THE INVENTION

Figure 1A:
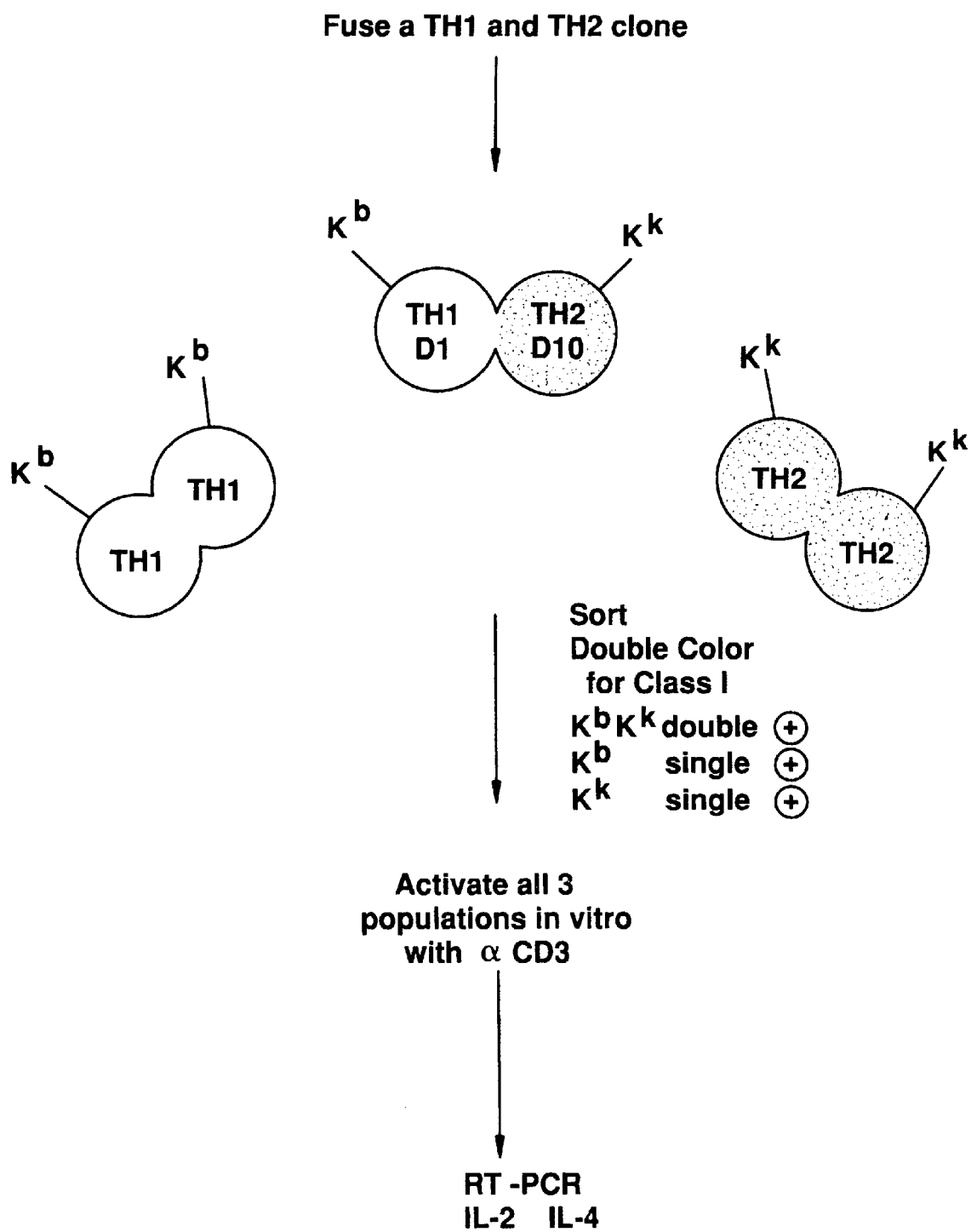
FIG. 1A is a schematic of the cell fusion approach used to demonstrate that cytokine expression is not due to a repressor

This invention pertains to methods and compositions for regulating T cell subsets by modulating transcription factor activity, as well as to screening assays for identifying compounds that can modulate such transcription factor activity. The invention is based, at least in part, on the discovery that Th2-specific expression of the interleukin-4 gene does not result from the action of a specific repressor protein (as shown in Example 1) but rather from the action of a specific transactivator protein. As described further herein, the transcription factor responsible for Th2-specific expression of the interleukin-4 gene has now been identified as the c-Maf proto-oncoprotein, which is selectively expressed in differentiating and mature Th2 cells and absent from Th1 cells (see Example 2). Ectopic expression of c-Maf in cells that do not normally express it (such as Th1 cells and B cells) leads to transactivation of the IL-4 promoter (see Example 3) and, under appropriate conditions, to production of endogenous IL-4 (see Example 4). Moreover, a protein present in nuclear extracts of Th2 cells, but not Th1 cells, footprints the IL-4 promoter in the region of a maf response element (MARE) (see Example 5) and recombinant c-Maf binds to the IL-4 promoter in vitro (see Example 6). The ability of c-Maf to transactivate IL-4 maps to the MARE and Th2-specific footprint in the IL-4 promoter (see Example 7).

The maf family of proteins is a sub-family of AP-1/CREB/ATF proteins. The v-maf oncogene was originally isolated from a spontaneous musculoaponeurotic fibrosarcoma of chicken and identified as the transforming gene of the avian retrovirus, AS42 (Nishizawa, M. et al. (1989) *Proc Natl. Acad. Sci. USA* 86:7711–7715). V-maf encodes a 42 kd basic region/leucine zipper (b-zip) protein with homology to the c-fos and c-jun oncogenes. Its cellular homologue, the c-maf proto-oncogene has only two structural changes in the coding region from v-maf(Kataoka, K. et al. (1993) *J. Virol.* 67:2133–2141). The maf family includes c-maf majB, a human retina-specific gene Nrl (Swaroop, A. et al (1992)

*Proc. Natl. Acad. Sci. USA* 89:266–270), mafk, mafF, mafF, mafG and p18. The latter four, mafK, mafF, mafG and p18, each encode proteins that lack the amino terminal two thirds of c-Maf that contains the transactivating domain (Fujiwara, K. T. et al. (1993) *Oncogene* 8:2371–2380; Igarashi, K. et al. (1995) *J. Biol. Chem.* 270:7615–7624; Andrews, N. C. et al. (1993) *Proc. Natl. Acad. Sci. USA* 90:11488–11492; Kataoka, K. et al. (1995) *Mol. Cell. Biol.* 15:2180–2190) and are referred to herein as "small" mafs. C-maf and maf family members form homodimers and heterodimers with each other and with Fos and Jun, consistent with the known ability of the AP-1 proteins to pair with each other (Kerppola, T. K. and Curran, T. (1994) *Oncogene* 9:675–684; Kataoka, K. et al. (1994) *Mol. Cell. Biol.* 14:700–712). The DNA target sequence to which c-Maf homodimers bind, termed the c-Maf response element (MARE), is a 13 or 14 bp element which contains a core TRE (T-MARE) or CRE (C-MARE) palindrome respectively. Prior to the present invention, little was known about the function of maf family members, although c-Maf has been shown to stimulate transcription from the Purkinje neuron-specific promoter L7 (Kurscher, C. and Morgan, J. I. (1994) *Mol. Cell. Biol.* 15:246–254) and Nrl has been shown to drive expression of the QR1 retina-specific gene (Swaroop, A. et al. (1992) *Proc. Natl. Acad. Sci. USA* 89:266–270). The small mafs have been shown to function as repressors of α and β-globin transcription when bound as homodimers but are essential as heterodimeric partners with the erythroid-specific factor p45NF-E2 to activate globin gene transcription (Kataoka, K. et al. (1995) *Mol. Cell. Biol.* 15:2180–2190; Igarashi, K. et al. (1994) *Nature* 367:568–572). MafK overexpression has been shown to induce erythroleukemia cell differentiation (Igarashi, K. et al. (1995) *Proc. Natl. Acad. Sci. USA* 92:7445–7449). However, prior to the present invention, there have been no reports implicating c-maf or maf family members in the regulation of genes expressed in lymphoid cells or in cytokine gene expression in any tissue.

Various aspects of the present invention are described in further detail in the following subsections.

I. Modulation of Th2-Associated Cytokine Production

As discussed above, the transcription factor responsible for the Th2-specific expression of the interleukin-4 gene has now been identified as the c-Maf proto-oncogene. Modulation of the expression and/or activity of c-Maf, therefore, provides a means to regulate the production of interleukin-4. Since IL-4 itself serves an autoregulatory function in the development of Th2 cells (see e g., Paul, W. E. and Seder, R. A. (1994) *Cell* 76:241–251; Seder, R. A. and Paul, W. E. (1994) *Ann. Rev. Immunol.* 12:635–673), and thus production of IL-4 can lead to the production of additional Th2-associated cytokines such as IL-5, IL-10 and IL-13 through further Th2 differentiation, modulation of c-Maf expression and/or activity provides a general approach for modulating production of Th2-associated cytokines.

Accordingly, the invention provides a method for modulating production of a Th2-associated cytokine by a cell. This method involves contacting the cell with an agent that modulates the activity of a transcription factor that regulates expression of a Th2-associated cytokine gene such that production of the Th2-associated cytokine by a cell is modulated. In particular, the modulatory agents of the invention are characterized by acting intracellularly to modulate the activity of a transcription factor. Preferably, the transcription factor is a member of the maf family and most preferably is c-Maf. As used herein, the term "Th2-associated cytokine" is intended to refer to a cytokine that is produced preferentially or exclusively by Th2 cells rather than by Th1 cells. Preferably the Th2-associated cytokine is interleukin-4. As used herein, the term "contacting" (ie., contacting a cell with an agent) is intended to include incubating the agent and the cell together in vitro (e.g., adding the agent to cells in culture) and administering the agent to a subject such that the agent and cells of the subject are contacted in vivo. As used herein, the various forms of the term "modulation" are intended to include stimulation (e.g., increasing or upregulating a particular response or activity) and inhibition (e.g., decreasing or downregulating a particular response or activity). Accordingly, in one embodiment of the method of the invention, production of a Th2-associated cytokine by the cell is stimulated by contacting the cell with a stimulatory agent that stimulates c-Maf expression and/or activity. In another embodiment of the method of the invention, production of a Th2-associated cytokine by the cell is inhibited by contacting the cell with a inhibitory agent that inhibits c-Maf expression and/or activity.

As demonstrated in the Examples, although c-Maf is responsible for the tissue specificity of IL-4 gene expression, c-Maf acts synergistically with one or more additional transcription factors to activate IL-4 gene transcription. In particular, c-Maf acts synergistically with an NF-AT protein to stimulate IL-4 gene expression. Moreover, NF-AT proteins and other members of the AP-1/CREB/ATF family of transcription factors have been demonstrated to be involved in regulating expression of both Th1- and Th2-associated cytokine genes. Accordingly, the method of the invention for modulating Th2-associated cytokine production by a cell can further comprise contacting the cell with a second agent that modulates (i.e., stimulates or inhibits) the expression or activity of a second transcription factor that contributes to regulating the expression of a Th1- or Th2-associated cytokine gene (discussed further below).

A. Stimulatory Agents

According to the method of the invention, to stimulate Th2-associated cytokine production by a cell, the cell is contacted with a stimulatory agent that stimulates expression and/or activity of a transcription factor (e.g., c-Maf) that regulates expression of a Th2-associated cytokine gene. Th2-associated cytokine production can be stimulated in cell types that do not normally express such cytokines, such as Th1 cells, B cells or non-lymphoid cells. Furthermore, Th2-associated cytokine production can be stimulated in helper precursor cells (Thp) to promote their differentiation along the Th2 pathway instead of the Th1 pathway.

A preferred stimulatory agent is a nucleic acid molecule encoding a maf family protein, wherein the nucleic acid molecule is introduced into the cell in a form suitable for expression of the maf family protein in the cell. For example, a c-Maf cDNA is cloned into a recombinant expression vector and the vector is transfected into the cell. As demonstrated in Example 3, ectopic expression of a c-mafrecombinant expression vector in Th1 cells, B cells or non-lymphoid cells leads to activation of the IL-4 promoter. Additionally, under appropriate conditions (discussed in further detail below), transcription of the endogenous IL-4 gene is stimulated, leading to IL-4 production by cells that do not normally express this cytokine (see Example 4).

To express a maf family protein in a cell, typically a maf family cDNA is first introduced into a recombinant expression vector using standard molecular biology techniques. A maf family cDNA can be obtained, for example, by amplification using the polymerase chain reaction (PCR) or by screening an appropriate cDNA library. The nucleotide sequences of maf family cDNAs are known in the art and can be used for the design of PCR primers that allow for amplification of a cDNA by standard PCR methods or for the design of a hybridization probe that can be used to screen a cDNA library using standard hybridization methods. Preferably, the maf family cDNA is that of the c-maf proto-oncogene. The nucleotide and predicted amino acid sequences of a mammalian (mouse) c-maf cDNA are disclosed in Kurscher C. and Morgan, J. I. (1995) *Mol. Cell. Biol.* 15:246–254 and deposited in the GenBank database at accession number S74567. This mammalian c-maf is highly homologous to the avian v-maf sequence (disclosed in Nishizawa, M. K. et al. (1989) *Proc. Natl. Acad. Sci USA* 86:7711–7715 and GenBank accession numbers D28598 and D28596), indicating that c-maf is well conserved among species. c-maf cDNAs from other mammalian species, including humans, can be isolated using standard molecular biology techniques (e.g., PCR or cDNA library screening) and primers or probes designed based upon the mouse or avian sequences. Human partial cDNA sequences homologous to the mouse c-maf cDNA are also deposited in the GenBank database at accession numbers H24189 and N75504. The sequences of other maf family members are also known in the art, for example MafB (Kataoka, K. et al (1994) *Mol. Cell. Biol.* 14:7581–91; GenBank accession number D28600), MafG (Kataoka et al. (1994) *Mol. Cell. Biol.* 14:7581–91; GenBank accession numbers D28601 and D28602), MafF (GenBank accession number D16184) and MafK (Igarashi, K. et al. (1995) *J. Biol Chem.* 270:7615–7624; GenBank accession numbers D16187 and D42124).

Following isolation or amplification of aintroducely cDNA, the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid in a form suitable for expression of the nucleic acid in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif.(1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g., inducible regulatory sequences). It will be appreciated by those skilled in the art that the design of the expression vector may depend on such factors as the choice of the host cell to be transformed, the level of expression of protein desired, etc. When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) *Nature* 329:840) and pMT2PC (Kaufman et al. (1987), *EMBO J.* 6:187–195). A variety of mammalian expression vectors carrying different regulatory sequences are commercially available. For constitutive expression of the nucleic acid in a mammalian host cell, a preferred regulatory element is the cytomegalovirus promoter/enhancer. Moreover, inducible regulatory systems for use in mammalian cells are known in the art, for example systems in which gene expression is regulated by heavy metal ions (see e.g. Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, e.d. Nouer, L., CRC, Boca Raton, Fla., pp167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual,* 2nd Edition, Cold Spring Harbor Laboratory press (1989)), and other laboratory manuals.

For stable transfection of mammalian cells, it is known that, depending, upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on a separate vector from that encoding a maf family protein or, more preferably, on the same vector. Cells stably transfected with the introduced nucleic acid can be identified by drug selection (e.g., cells that have incorporated the selectable marker gene will survive, while the other cells die).

Another form of a stimulatory agent for stimulating expression of a Th2-associated cytokine in a cell is a chemical compound that stimulates the expression or activity of an endogenous maf family protein in the cell. Such compounds can be identified using screening assays that select for compounds that stimulate the expression or activity of a maf family protein. Examples of suitable screening assays are described in further detail in subsection V below.

In addition to use of an agent that stimulates the expression or activity of a maf family protein, the stimulatory methods of the invention can involve the use of a second agent that stimulates the expression or activity of a second transcription factor that contributes to regulating the expression of a Th1- or Th2-associated cytokine gene. In Example 4, it is shown that stimulation of the expression of endogenous IL-4 in M12 B lymphoma cells required the introduction into the cells of both a c-Maf expression vector and an NF-AT expression vector, thereby demonstrating that c-Maf and NF-AT act synergistically to activate IL-4 transcription, with c-maf responsible for the tissue-specificity of expression. While the skilled artisan will appreciate that certain cells may express sufficient amounts of endogenous NF-AT such that use of a second agent that stimulates the expression or activity of NF-AT is unnecessary, in certain situations and with certain cell types it may be necessary to stimulate both c-Maf and NF-AT to achieve IL-4 production.

Accordingly, in one embodiment, the stimulatory methods of the invention involve the use of a first agent that stimulates the expression or activity of c-Maf and a second agent that stimulates the expression or activity of an NF-AT protein. A preferred second agent for stimulating NF-AT activity in a cell is a recombinant expression encoding an NF-AT, wherein the recombinant expression vector is introduced into the cell and NF-AT is expressed in the cell. NF-AT-encoding expression vectors can be prepared and introduced into cells as described above for c-Maf expression vectors. The nucleotide sequences of NF-AT cDNAs are known in the art and can be used for the design of PCR primers that allow for amplification of a cDNA by standard PCR methods or for the design of a hybridization probe that can be used to screen a cDNA library using standard hybridization methods. Four NF-AT family members have been identified (see e.g., Emmel, E. A. et al. (1989) *Science* 246:1617–1620; Flanagan, W. M. et al. (1991) *Nature* 352:803–807; Jain, J. et al. (1993) *Nature* 365:352–355; McCaffrey, P. G. et al. (1993) *Science* 262:750–754; Rao, A. (1994) *ImmunoL Today* 15:274–281; Northrop, J. P. et al. (1994) *Nature* 369:497). Preferably, the NF-AT cDNA is that of NF-ATp. The nucleotide and predicted amino acid sequences of a mammalian NF-ATp cDNA are disclosed in McCaffrey, P. G. et al. (1993) *Science* 262:750–754. The nucleotide and predicted amino acid sequences of a mammalian NF-ATc cDNA are disclosed in Northrop, J. P. et al. (1994) *Nature* 369:497 and deposited in the GenBank database at accession number U08015. The nucleotide and predicted amino acid sequences of mammalian NF-AT3 and NF-AT4 cDNAs are disclosed in Hoey, T. et al. (1995) *Immunity* 2:461–472.

Alternative to use of an NF-AT cDNA to stimulate the activity of NF-AT in a cell, one or more chemical compounds that stimulate NF-AT activity in a cell can be used as a second agent in a stimulatory method of the invention. Compounds that stimulate NF-AT activity in cells are known in the art (for a review see Rao, A. (1994) *Immunol. Today* 15:274–281). For example, stimulation of certain cells with the phorbol ester phorbol myristate acetate (PMA) and a calcium ionophore (e.g., ionomycin) results in translocation of NF-ATs to the cell nucleus (see e.g., Flanagan, W. M. et al. (1991) *Nature* 352:803–807; Jain, J. et al. (1993) *Nature* 365:352–355). Additionally, stimulation of T cells through the T cell receptor (TcR), for example with an anti-CD3 antibody, results in activation of NF-AT in the T cells.

In addition to NF-AT proteins, AP-1 family members, including c-Jun, c-Fos, Fra-1, Fra-2, Jun B and Jun D, have been shown to be involved in regulating the expression of both Th1- and Th2-associated cytokine genes (e.g., IL-2 and IL-4)(see e.g., Rao, A. et al. (1994) *Immunol. Today* 15:274–281; Jain, J. et al. (1993) *Nature* 365:352–355; Boise, L. H. et al. (1993) *Mol. Cell. Biol.* 13:1911–1919; Rooney, J. et al. (1995) *Immunity* 2:545–553; Rooney, J. et al. (1995) *Mol. Cell. Biol.* 15:6299–6310). Although these factors are not responsible for the Th1/Th2 specificity of expression of the cytokine genes, and these factors do not appear to synergize with c-Maf in regulating IL-4 gene expression (see the Examples), AP-1 family members have been shown to increase IL-4 expression in Th2 cells (see e.g., Rooney, J. et al. (1995) *Immunity* 2:545–553). Accordingly, in certain circumstances it may be beneficial, in addition to stimulating c-Maf activity (and possibly NF-AT activity), also to stimulate the activity of an AP-1 protein. Accordingly, in one embodiment, the stimulatory methods of the invention involve the use of a first agent that stimulates the expression or activity of c-Maf and a second agent that stimulates the expression or activity of an AP-1 protein. In another embodiment, the invention involves the use of a first agent that stimulates the expression or activity of c-Maf, a second agent that stimulates the expression or activity of an NF-AT protein and a third agent that stimulates the expression or activity of an AP-1 protein.

A preferred agent for stimulating AP-1 activity in a cell is a recombinant expression encoding an AP-1 protein, wherein the recombinant expression vector is introduced into the cell and the AP-1 protein is expressed in the cell. AP-1-encoding expression vectors can be prepared and introduced into cells as described above for c-Maf expression vectors. The nucleotide sequences of AP-1 cDNAs are known in the art. For example, the nucleotide and predicted amino acid sequences of human c-fos are disclosed in van Straaten, F. et al. (1983) *Proc. Natl. Acad. Sci. USA* 80:3183–3187. The nucleotide and predicted amino acid sequences of human c-jun are disclosed in Bohmann, D. et al. (1987) *Science* 238:1386–1392. The nucleotide and predicted amino acid sequences of human jun-B and jun-D are disclosed in Nomura, N. et al. (1990) *Nucl. Acids Res.* 18:3047–3048. The nucleotide and predicted amino acid sequences of human fra-1 and fra-2 are disclosed in Matsui, M. et al. (1990) *Oncogene* 5:249–255. These sequences can be used for the design of PCR primers that allow for amplification of a cDNA by standard PCR methods or for the design of a hybridization probe that can be used to screen a cDNA library using standard hybridization methods. Alternatively, one or more chemical compounds that stimulate AP-1 activity in a cell can be used as additional agents in a stimulatory method of the invention. Compounds that stimulate AP-1 activity in cells are known in the art, including PMA/calcium ionophore (e.g., ionomycin) and anti-CD3 antibodies.

B. Inhibitory Agents

According to the method of the invention, to inhibit Th2-associated cytokine production by a cell, the cell is contacted with an inhibitory agent that inhibits expression and/or activity of a transcription factor (e.g., c-Maf) that regulates expression of a Th2-associated cytokine gene. Th2-associated cytokine production can be inhibited in, for example, Th2 cells or in helper precursor cells (Thp) to promote their differentiation along the Th1 pathway instead of the Th2 pathway. Inhibitory agents of the invention can be, for example, intracellular binding molecules that act to inhibit the expression or activity of the transcription factor. As used herein, the term "intracellular binding molecule" is intended to include molecules that act intracellularly to inhibit the expression or activity of a protein by binding to the protein or to a nucleic acid (e.g., an mRNA molecule) that encodes the protein. Examples of intracellular binding molecules, described in further detail below, include antisense nucleic acids, intracellular antibodies and dominant negative inhibitors.

In one embodiment, an inhibitory agent of the invention is an antisense nucleic acid molecule that is complementary to a gene encoding a maf family protein, or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. J. Med.* 334:316–318; Bennett, M. R. and Schwartz, S. M. (1995) *Circulation* 92:1981–1993; Mercola, D. and Cohen, J. S. (1995) *Cancer Gene Ther.* 2:47–59; Rossi, J. J. (1995) *Br. Med. Bull.* 51:217–225; Wagner, R. W. (1994) *Nature* 372:333–335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the MRNA, for instance a transcription initiation sequence or regulatory element. Preferably, an antisense nucleic acid is designed so as to be complementary to a region preceding or spanning the initiation codon on the coding strand or in the 3' untranslated region of an MRNA. An antisense nucleic acid for inhibiting the expression of a Maf family protein in a cell can be designed based upon the nucleotide sequence encoding the Maf family protein, constructed according to the rules of Watson and Crick base pairing.

An antisense nucleic acid can exist in a variety of different forms. For example, the antisense nucleic acid can be an oligonucleotide that is complementary to only a portion of a maf family gene. An antisense oligonucleotides can be constructed using chemical synthesis procedures known in the art. An antisense oligonucleotide can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit Maf protein expression in cells in culture, one or more antisense oligonucleotides can be added to cells in culture media, typically at 200 $\mu$g oligonucleotide/ml.

Alternatively, an antisense nucleic acid can be produced biologically using an expression vector into which a nucleic acid has been subcloned in an antisense orientation (i e, nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared as described above for recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique, as described above for recombinant expression vectors.

In another embodiment, an antisense nucleic acid for use as an inhibitory agent is a ribozyme. Ribozymes are catalytic RNA molecules with ribonuclease activity which are capable of cleaving a single-stranded nucleic acid, such as an MRNA, to which they have a complementary region (for reviews on ribozymes see e.g., Ohkawa, J. et al. (1995) *J. Biochem.* 118:251–258; Sigurdsson, S. T. and Eckstein, F. (1995) *Trends Biotechnol* 13:286–289; Rossi, J. J. (1995) *Trends Biotechnol* 13:301–306; Kiehntopf, M. et al. (1995) *J. Mol. Med.* 73:65–71). A ribozyme having specificity for a maf family mRNA can be designed based upon the nucleotide sequence of the maf family, preferably c-maf. For example, a derivative of a Tetrahymena L-19 IVS RNA can be constructed in which the base sequence of the active site is complementary to the base sequence to be cleaved in a c-mafmRNA. See for example U.S. Pat. Nos. 4,987,071 and 5,116,742, both by Cech et al. Alternatively, c-maf mRNA can be used to select a catalytic RNA having a specific ribonuclease activity from a pool of RNA molecules. See for example Bartel, D. and Szostak, J. W. (1993) *Science* 261: 1411–1418.

Another type of inhibitory agent that can be used to inhibit the expression and/or activity of a Maf protein in a cell is an intracellular antibody specific for the Maf protein. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al. (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the inhibitory methods of the invention, preferably an intracellular antibody that specifically binds the transcription factor is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca, S. et al. (1990) *EMBO J.* 9:101–108; Mhashilkar, A. M. et al. (1995) *EMBO J.* 14:1542–1551). A preferred nuclear localization signal to be used for nuclear targeting of the intracellular antibody chains is the nuclear localization signal of SV40 Large T antigen (see Biocca, S. et al. (1990) *EMBO J.* 9:101–108; Mhashilkar, A. M. et al. (1995) *EMBO J.* 14:1542–1551).

To prepare an intracellular antibody expression vector, antibody light and heavy chain cDNAs encoding antibody chains specific for the target protein of interest, e.g., a Maf family protein, are isolated, typically from a hybridoma that secretes a monoclonal antibody specific for the maf protein. Preparation of antisera against Maf family proteins has been described in the art (see e.g., Fujiwara, K. T. et al. (1993) *Oncogene* 8:2371–2380; Kataoka, K. et al. (1993) *J. Virol.* 67:2133–2141; Kerppola, T. K. and Curran, T. (1994) *Oncogene* 9:675–684; Igarashi, K et al. (1995) *Proc. Natl. Acad. Sci. USA* 92:7445–7449). Anti-Maf protein antibodies can be prepared by immunizing a suitable subject, (e.g., rabbit, goat, mouse or other mammal) with a Maf protein immunogen. An appropriate immunogenic preparation can contain, for examples, recombinantly expressed Maf protein or a chemically synthesized Maf peptide. The preparation can further include an adjuvant, such as Freund's complete or incomplete adjuvant, or similar immunostimulatory agent. Antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387–402; M. L. Gefter et al. (1977) *Somatic Cell Genet.,* 3:23136). Briefly, an immortal cell line (typically a myeloma) is fused to lymphocytes (typically splenocytes) from a mammal immunized with a maf protein immunogen as described above, and the culture supernatants of the resulting hybridoma cells are screened to identify a hybridoma producing a monoclonal antibody that binds specifically to the Maf protein. Any of the many well known protocols used for fusing lymphocytes and immortalized cell lines can be applied for the purpose of generating an anti-Maf protein monoclonal antibody (see, e.g., G. Galfre et al. (1977) *Nature* 266:550–52; Gefter et al. *Somatic Cell Genet.*, cited supra; Lerner, *Yale J. Biol. Med.*, cited supra; Kenneth, Monoclonal Antibodies, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the maf protein are identified by screening the hybridoma culture supernatants for such antibodies, e.g., using a standard ELISA assay.

Alternative to preparing monoclonal antibody-secreting hybridomas, a monoclonal anti-maf antibody can be identified and isolated by screening a recombinant combinatorial immunoglobulin library (e.g., an antibody phage display library) with a maf protein or peptide to thereby isolate immunoglobulin library members that bind specifically to a Maf protein. Kits for generating and screening phage display libraries are commercially available (e.g., the Pharmacia *Recombinant Phage Antibody System*, Catalog No. 27-9400-01; and the Stratagene SurfZIP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J.*

12:725–734; Hawkins et al (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Once a monoclonal antibody specific for the Maf protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a fIll-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit transcription factor activity in a cell, the expression vector encoding the transcription factor-specific intracellular antibody is introduced into the cell by standard transfection methods, as discussed hereinbefore.

Yet another form of an inhibitory agent of the invention is an inhibitory form of a Maf protein, also referred to herein as a dominant negative inhibitor. The maf family of proteins are known to homodimerize and to heterodimerize with other AP-1 family members, such as Fos and Jun (see e.g., Kerppola, T. K. and Curran, T. (1994) *Oncogene* 9:675–684; Kataoka, K. et al. (1994) *Mol. Cell. Biol.* 14:700–712). One means to inhibit the activity of transcription factors that form dimers is through the use of a dominant negative inhibitor that has the ability to dimerize with functional transcription factors but that lacks the ability to activate transcription (see e.g., Petrak, D. et al. (1994) *J. Immunol.* 153:2046–2051). By dimerizing with functional transcription factors, such dominant negative inhibitors can inhibit their functional activity. This process may occur naturally as a means to regulate gene expression. For example, there are a number of "small" maf proteins, such as mafK, mafF, mafG and p18, which lack the amino terminal two thirds of c-Maf that contains the transactivating domain (Fujiwara, K. T. et al. (1993) *Oncogene* 8:2371–2380; Igarashi, K. et al. (1995) *J. Biol. Chem.* 270:7615–7624; Andrews, N. C. et al. (1993) *Proc. Natl. Acad. Sci. USA* 90:11488–11492; Kataoka, K. et al. (1995) *Mol. Cell. Biol.* 15:2180–2190). Homodimers of the small maf proteins act as negative regulators of transcription (Igarashi, K. et al. (1994) *Nature* 367:568–572) and three of the small maf proteins (MafK, MafF and MafG) have been shown to competitively inhibit transactivation mediated by the v-Maf oncoprotein (Kataoka, K. et al. (1996) *Oncogene* 12:53–62). Additionally, MafB has been identified as an interaction partner of Ets-1 and shown to inhibit Ets-1-mediated transactivation of the transferrin receptor and to inhibit erythroid differentiation (Sieweke, M. H. et al. (1996) *Cell* 85:49–60).

Accordingly, an inhibitory agent of the invention can be a form of a Maf protein that has the ability to dimerize with c-Maf but that lacks the ability to activate transcription. This dominant negative form of a Maf protein may be, for example, a small Maf protein (e.g., MafK, MafF, MafG) that naturally lacks a transactivation domain, MafB or a mutated form of c-Maf in which the transactivation domain has been removed. Such dominant negative Maf proteins can be expressed in cells using a recombinant expression vector encoding the Maf protein, which is introduced into the cell by standard transfection methods. To express a mutant form of c-Maf lacking a transactivation domain, nucleotide sequences encoding the amino terminal transactivation domain of c-Maf are removed from the c-maf cDNA by standard recombinant DNA techniques. Preferably, at least amino acids 1–122 are removed. More preferably, at least amino acids 1–187, or amino acids 1–257, are removed. Nucleotide sequences encoding the basic-leucine zipper region are maintained. The truncated cDNA is inserted into a recombinant expression vector, which is then introduced into a cell to allow for expression of the truncated c-maf, lacking a transactivation domain, in the cell.

Yet another type of inhibitory agent that can be used to inhibit the expression and/or activity of a maf protein in a cell is chemical compound that inhibits the expression or activity of an endogenous maf family protein in the cell. Such compounds can be identified using screening assays that select for compounds that inhibit the expression or activity of a maf family protein. Examples of suitable screening assays are described in further detail in subsection V below.

As discussed above with regard to stimulatory agents, the inhibitory methods of the invention can involve the use of one or more additional inhibitory agents that inhibit the expression or activity of one or more additional transcription factors that contributes to regulating the expression of a Th1- or Th2-associated cytokine gene. For example, in one embodiment, the inhibitory method of the invention comprises contacting a cell with a first agent that inhibits the expression or activity a maf family protein and a second agent that inhibits the expression or activity of an NF-AT protein. In another embodiment, the inhibitory method of the invention comprises contacting a cell with a first agent that inhibits the expression or activity a maf family protein and a second agent that inhibits the expression or activity of an AP-1 protein. In yet another embodiment, the inhibitory method of the invention comprises contacting a cell with a first agent that inhibits the expression or activity a maf family protein, a second agent that inhibits the expression or activity of an NF-AT protein and a third agent that inhibits the expression or activity of an AP-1 protein. Examples of types of inhibitory agents for inhibiting NF-AT or AP-1 proteins include antisense nucleic acids, intracellular antibodies, dominant negative inhibitors and chemical compounds that inhibit the endogenous proteins, as described above. Regarding the latter, it is known in the art that the nuclear translocation of NF-ATp is inhibited by the immunosuppressive drugs cyclosporin A and FK506 (see e.g., Rao, A. (1994) *Immunol. Today* 15:274–281; Rao, A. (1995) *J. Leukoc. Biol.* 57:536–542). Accordingly, in one embodiment of the inhibitory method, an immunosuppressive drug such as cyclosporin A or FK506 (or other related drug that inhibits the calcineurin pathway) is used in combination with an agent that inhibits the expression or activity of c-Maf.

The method of the invention for modulating production of Th2-associated cytokines by a cell can be practiced either in vitro or in vivo (the latter is discussed further in the following subsection). For practicing the method in vitro, cells can be obtained from a subject by standard methods and incubated (ie., cultured) in vitro with a stimulatory or inhibitory agent of the invention to stimulate or inhibit, respectively, the production of Th2-associated cytokines. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells or B cells can be enriched or depleted, for example, by positive and/or negative selection using antibodies to T cell or B cell surface markers, for example by incubating cells with a specific primary monoclonal antibody (mAb), followed by isolation of cells that bind the mAb using magnetic beads coated with a secondary antibody that binds the primary mAb. Peripheral blood or bone marrow derived hematopoietic stem cells can be isolated by similar techniques using stem cell-specific mabs (e.g., anti-CD34 mabs). Specific cell populations can also be isolated by fluoresence activated cell sorting according to standard methods. Monoclonal antibodies to cell-specific surface markers known in the art and many are commercially available.

When a stimulatory agent is used in vitro, resulting in stimulation of the production of Th2-associated cytokines, in particular IL-4, the cytokine(s) can be recovered from the culture supernatant for further use. For example, the culture supernatant, or a purified fraction thereof, can be applied to T cells in culture to influence the development of Th1 or Th2 cells in vitro. Alternatively, the culture supernatant, or a purified fraction thereof, can be administered to a subject to influence the development of Th1 vs. Th2 responses in the subject.

Moreover, cells treated in vitro with either a stimulatory or inhibitory agent can be administered to a subject to influence the development of a Th1 vs. Th2 response in the subject. Accordingly, in another embodiment, the method of the invention for modulating the production of Th2-associated cytokines by a cell further comprises administering the cell to a subject to thereby modulate development of Th1 or Th2 cells in a subject. Preferred cell types for ex vivo modification and readministration include T cells, B cells and hematopoietic stem cells. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

II. Methods for Modulating Development of Th1 or Th2 Cells in a Subject

Another aspect of the invention pertains to a method for modulating development of Th1 or Th2 cells in a subject. The term "subject" is intended to include living organisms in which an immune response can be elicited. Preferred subjects are mammals. Examples of subjects include humans, monkeys, dogs, cats, mice, rats, cows, horses, goats and sheep. As discussed above, one way to modulate Th1/Th2 ratios in a subject is to treat cells (e.g., T cells, B cells or hematopoietic stem cells) ex vivo with one or more modulatory agents of the invention, such that production of a Th2-associated cytokine by the cells is modulated, followed by administration of the cells to the subject. In another embodiment, Th1/Th2 ratios are modulated in a subject by administering to the subject an agent that modulates the activity of a transcription factor that regulates expression of a Th2-associated cytokine gene such that development of Th1 or Th2 cells in the subject is modulated. Preferably, the transcription factor is a maf family protein and most preferably a c-Maf protein. Preferably, the Th2-associated cytokine is IL-4. Development of a Th2 response in the subject can be promoted by administration of one or more stimulatory agents of the invention, whereas development of a Th1 response in the subject can be promoted by administration of one or more inhibitory agents of the invention. As discussed above, in certain situations it may be desirable, in addition to modulating the activity of a maf family protein, to also modulate the activity of other transcription factors involved in regulating Th1- or Th2-associated cytokine genes. Preferably, the activity of an NF-AT protein(s) is also modulated. Additionally or alternatively, the activity of an AP-1 protein(s) is also modulated.

For stimulatory or inhibitory agents that comprise nucleic acids (including recombinant expression vectors encoding transcription factors, antisense RNA, intracellular antibodies or dominant negative inhibitors), the agents can be introduced into cells of the subject using methods known in the art for introducing nucleic acid (e.g., DNA) into cells in vivo. Examples of such methods include:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes (Herz and Gerard (1993) Proc. Natl. Acad Sci. USA 90:2812–2816) and muscle cells (Quantin et al. (1992) Proc. Natl. Acad. Sci. USA 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin etaL. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay.

A modulatory agent, such as a chemical compound that stimulates or inhibits endogenous c-Maf activity, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

III. Applications of the Methods of the Invention

Identification of the transcription factor that controls the production of IL-4, and hence continued formation of Th2 cells, allows for selective manipulation of T cell subsets in a variety of clinical situations using the modulatory methods of the invention. The stimulatory methods of the invention (i.e., methods that use a stimulatory agent) result in production of Th2-associated cytokines, with concomitant promotion of a Th2 response and downregulation of a Th1 response. In contrast, the inhibitory methods of the invention (i.e., methods that use an inhibitory agent) inhibit the production of Th2-associated cytokines, with concomitant downregulation of a Th2 response and promotion of a Th1 response. Thus, to treat a disease condition wherein a Th2 response is beneficial, a stimulatory method of the invention is selected such that Th2 responses are promoted while downregulating Th1 responses. Alternatively, to treat a disease condition wherein a Th1 response is beneficial, an inhibitory method of the invention is selected such that Th2 responses are downregulated while promoting Th1 responses. Application of the methods of the invention to the treatment of disease conditions may result in cure of the condition, a decrease in the type or number of symptoms associated with the condition, either in the long term or short term (i. e., amelioration of the condition) or simply a transient beneficial effect to the subject.

Numerous disease conditions associated with a predominant Th1 or Th2-type response have been identified and could benefit from modulation of the type of response mounted in the individual suffering from the disease condition. Application of the immunomodulatory methods of the invention to such diseases is described in further detail below.

A. Allergies

Allergies are mediated through IgE antibodies whose production is regulated by the activity of Th2 cells and the cytokines produced thereby. In allergic reactions, IL-4 is produced by Th2 cells, which further stimulates production of IgE antibodies and activation of cells that mediate allergic reactions, i e., mast cells and basophils. IL-4 also plays an important role in eosinophil mediated inflammatory reactions. Accordingly, the inhibitory methods of the invention can be used to inhibit the production of Th2-associated cytokines, and in particular IL-4, in allergic patients as a means to downregulate production of pathogenic IgE antibodies. An inhibitory agent may be directly administered to the subject or cells (e.g., Thp cells or Th2 cells) may be obtained from the subject, contacted with an inhibitory agent ex vivo, and readministered to the subject. Moreover, in certain situations it may be beneficial to coadminister to the subject the allergen together with the inhibitory agent or cells treated with the inhibitory agent to inhibit (e.g., desensitize) the allergen-specific response. The treatment may be further enhanced by administering other Th1-promoting agents, such as the cytokine IL-12 or antibodies to Th2-associated cytokines (e.g., anti-IL-4 antibodies), to the allergic subject in amounts sufficient to further stimulate a Th1-type response.

B. Cancer

The expression of Th2-promoting cytokines has been reported to be elevated in cancer patients (see e.g., Yamamura, M., et al. (1993) *J. Clin. Invest.* 91:1005–1010; Pisa, P., et al. (1992) *Proc. Natl. Acad. Sci USA* 89:7708–7712) and malignant disease is often associated with a shift from Th1 type responses to Th2 type responses along with a worsening of the course of the disease. Accordingly, the inhibitory methods of the invention can be used to inhibit the production of Th2-associated cytokines in cancer patients, as a means to counteract the Th1 to Th2 shift and thereby promote an ongoing Th1 response in the patients to ameliorate the course of the disease. The inhibitory method can involve either direct administration of an inhibitory agent to a subject with cancer or ex vivo treatment of cells obtained from the subject (e.g., Thp or Th2 cells) with an inhibitory agent followed by readministration of the cells to the subject. The treatment may be further enhanced by administering other Th1-promoting agents, such as the cytokine IL-12 or antibodies to Th2-associated cytokines (e.g., anti-IL-4 antibodies), to the recipient in amounts sufficient to further stimulate a Th1-type response.

C. Infectious Diseases

The expression of Th2-promoting cytokines also has been reported to increase during a variety of infectious diseases, including HIV infection, tuberculosis, leishmaniasis, schistosomiasis, filarial nematode infection and intestinal nematode infection (see e.g.; Shearer, G. M. and Clerici, M. (1992) *Prog. Chem. Immunol.* 54:21–43; Clerici, M and Shearer, G. M. (1993) *Immunology Today* 14:107–111; Fauci, A. S. (1988) *Science* 239:617623; Locksley, R. M. and Scott, P. (1992) *Immunoparasitology Today* 1:A58–A61; Pearce, E. J., et al. (1991) *J. Exp. Med.* 173:159–166; Grzych, J-M., et al. (1991) *J. Immunol.* 141:1322–1327; Kullberg, M. C., et al. (1992) *J. Immunol.* 148:3264–3270; Bancroft, A. J., et al. (1993) *J. Immunol.* 150:1395–1402; Pearlman, E., et al. (1993) *Infect. Immun.* 61:1105–1112; Else, K. J., et al. (1994) *J. Exp. Med.* 179:347–351) and such infectious diseases are also associated with a Th1 to Th2 shift in the immune response. Accordingly, the inhibitory methods of the invention can be used to inhibit the production of Th2-associated cytokines in subjects with infectious diseases, as a means to counteract the Th1 to Th2 shift and thereby promote an ongoing Th1 response in the patients to ameliorate the course of the infection. The inhibitory method can involve either direct administration of an inhibitory agent to a subject with an infectious disease or ex vivo treatment of cells obtained from the subject (e.g., Thp or Th2 cells) with an inhibitory agent followed by readministration of the cells to the subject. The treatment may be further enhanced by administering other Th1-promoting agents, such as the cytokine IL-12 or antibodies to Th2-associated cytokines (e.g., anti-IL-4 antibodies), to the recipient in amounts sufficient to further stimulate a Th1-type response.

D. Autoimmune Diseases

The stimulatory methods of the invention can be used therapeutically in the treatment of autoimmune diseases that are associated with a Th2-type dysfunction. Many autoimmune disorders are the result of inappropriate activation of T cells that are reactive against self tissue and that promote the production of cytokines and autoantibodies involved in the pathology of the diseases. Modulation of T helper-type responses can have an effect on the course of the autoimmune disease. For example, in experimental allergic encephalomyelitis (EAE), stimulation of a Th2-type response by administration of IL-4 at the time of the induction of the disease diminishes the intensity of the autoimmune disease (Paul, W. E., et al. (1994) *Cell* 76:241–251). Furthermore, recovery of the animals from the disease has been shown to be associated with an increase in a Th2-type response as evidenced by an increase of Th2-specific cytokines (Koury, S. J., et al. (1992) *J. Exp. Med.* 176:1355–1364). Moreover, T cells that can suppress EAE secrete Th2-specific cytokines (Chen, C., et al. (1994) *Immunity* 1:147–154). Since stimulation of a Th2-type response in EAE has a protective effect against the disease, stimulation of a Th2 response in subjects with multiple sclerosis (for which EAE is a model) is likely to be beneficial therapeutically.

Similarly, stimulation of a Th2-type response in type I diabetes in mice provides a protective effect against the disease. Indeed, treatment of NOD mice with IL-4 (which promotes a Th2 response) prevents or delays onset of type I diabetes that normally develops in these mice (Rapoport, M. J., et al. (1993) *J. Exp. Med.* 178:87–99). Thus, stimulation of a Th2 response in a subject suffering from or susceptible to diabetes may ameliorate the effects of the disease or inhibit the onset of the disease.

Yet another autoimmune disease in which stimulation of a Th2-type response may be beneficial is rheumatoid arthritis (RA). Studies have shown that patients with rheumatoid arthritis have predominantly Th1 cells in synovial tissue (Simon, A. K., et al., (1994) *Proc. Natl. Acad. Sci USA* 91:8562–8566). By stimulating a Th2 response in a subject with RA, the detrimental Th1 response can be concomitantly downmodulated to thereby ameliorate the effects of the disease.

Accordingly, the stimulatory methods of the invention can be used to stimulate production of Th2-associated cytokines in subjects suffering from, or susceptible to, an autoimmune disease in which a Th2-type response is beneficial to the course of the disease. The stimulatory method can involve either direct administration of a stimulatory agent to the subject or ex vivo treatment of cells obtained from the subject (e.g., Thp, Th1 cells, B cells, non-lymphoid cells) with a stimulatory agent followed by readministration of the cells to the subject. The treatment may be further enhanced by administering other Th2-promoting agents, such as IL-4 itself or antibodies to Th1-associated cytokines, to the subject in amounts sufficient to further stimulate a Th2-type response.

In contrast to the autoimmune diseases described above in which a Th2 response is desirable, other autoimmune diseases may be ameliorated by a Th1-type response. Such diseases can be treated using an inhibitory agent of the invention (as described above for cancer and infectious diseases). The treatment may be further enhanced by administrating a Th1-promoting cytokine (e.g., IFN-γ) to the subject in amounts sufficient to further stimulate a Th1-type response.

The efficacy of agents for treating autoimmune diseases can be tested in the above described animal models of human diseases (e.g., EAE as a model of multiple sclerosis and the NOD mice as a model for diabetes) or other well characterized animal models of human autoimmune diseases. Such animal models include the mrl/lpr/lpr mouse as a model for lupus erythematosus, murine collagen-induced arthritis as a model for rheumatoid arthritis, and murine experimental myasthenia gravis (see Paul ed., *Fundamental Immunology*, Raven Press, New York, 1989, pp. 840–856). A modulatory (ie., stimulatory or inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Non-limiting examples of autoimmune diseases and disorders having an autoimmune component that may be treated according to the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

E. Transplantation

While graft rejection or graft acceptance may not be attributable exclusively to the action of a particular T cell subset (i.e., Th1 or Th2 cells) in the graft recipient (for a discussion see Dallman, M. J. (1995) *Curr. Opin. Immunol.* 7:632–638), numerous studies have implicated a predominant Th2 response in prolonged graft survival or a predominant Th2 response in graft rejection. For example, graft acceptance has been associated with production of a Th2 cytokine pattern and/or graft rejection has been associated with production of a Th1 cytokine pattern (see e.g., Takeuchi, T. et al. (1992) *Transplantation* 53:1281–1291; Tzakis, A. G. et al. (1994) *J. Pediatr. Surg* 29:754–756; Thai, N. L. et al. (1995) Transplantation 59:274–281). Additionally, adoptive transfer of cells having a Th2 cytokine phenotype prolongs skin graft survival (Maeda, H. et al. (1994) *Int. Immunol.* 6:855–862) and reduces graft-versus-host disease (Fowler, D. H. et al. (1994) *Blood* 84:3540–3549; Fowler, D. H. et al. (1994) *Prog. Clin. Biol. Res.* 389:533–540). Still further, administration of IL-4, which promotes Th2 differentiation, prolongs cardiac allograft survival (Levy, A. E. and Alexander, J. W. (1995) *Transplantation* 60:405–406), whereas administration of IL-12 in combination with anti-IL-10 antibodies, which promotes Th1 differentiation, enhances skin allograft rejection (Gorczynski, R. M. et al. (1995) *Transplantation* 60:1337–1341).

Accordingly, the stimulatory methods of the invention can be used to stimulate production of Th2-associated cytokines in transplant recipients to prolong survival of the graft. The stimulatory methods can be used both in solid organ transplantation and in bone marrow transplantation (e.g., to inhibit graft-versus-host disease). The stimulatory method can involve either direct administration of a stimulatory agent to the transplant recipient or ex vivo treatment of cells obtained from the subject (e.g., Thp, Th1 cells, B cells, non-lymphoid cells) with a stimulatory agent followed by readministration of the cells to the subject. The treatment may be further enhanced by administering other Th2-promoting agents, such as IL-4 itself or antibodies to Th1-associated cytokines, to the recipient in amounts sufficient to further stimulate a Th2-type response.

In addition to the foregoing disease situations, the modulatory methods of the invention also are useful for other purposes. For example, the stimulatory methods of the invention (i.e., methods using a stimulatory agent) can be used to stimulate production of Th2-promoting cytokines (e.g., IL-4) in vitro for commercial production of these cytokines (e.g., cells can be contacted with the stimulatory agent in vitro to stimulate IL-4 production and the IL-4 can be recovered from the culture supernatant, further purified if necessary, and packaged for commercial use).

Furthermore, the modulatory methods of the invention can be applied to vaccinations to promote either a Th1 or a Th2 response to an antigen of interest in a subject. That is, the agents of the invention can serve as adjuvants to direct an immune response to a vaccine either to a Th1 response or a Th2 response. For example, to stimulate an antibody response to an antigen of interest (i e., for vaccination purposes), the antigen and a stimulatory agent of the invention can be coadministered to a subject to promote a Th2 response to the antigen in the subject, since Th2 responses provide efficient B cell help and promote IgG1 production. Alternatively, to promote a cellular immune response to an antigen of interest, the antigen and an inhibitory agent of the invention can be coadministered to a subject to promote a Th1 response to timmantigen in a subject, since Th1 responses favor the development of cell-mediated immune responses (e.g., delayed hypersensitivity responses). The antigen of interest and the modulatory agent can be formulated together into a single pharmaceutical composition or in separate compositions. In a preferred embodiment, the antigen of interest and the modulatory agent are administered simultaneously to the subject. Alternatively, in certain situations it may be desirable to administer the antigen first and then the modulatory agent or vice versa (for example, in the case of an antigen that naturally evokes a Th1 response, it may be beneficial to first administer the antigen alone to stimulate a Th1 response and then administer a stimulatory agent, alone or together with a boost of antigen, to shift the immune response to a Th2 response).

IV. Compositions for Modulating Th2-Associated Cytokine Production

Another aspect of the invention pertains to compositions that can be used to modulate Th2-associated cytokine production by a cell or Th1/Th2 development in a subject in accordance with the methods of the invention. The invention provides recombinant expression vectors comprising a nucleotide sequence encoding a maf family protein operatively linked to regulatory sequences that direct expression of the maf family protein specifically in certain cell types. In a preferred embodiment, the regulatory sequences direct expression of the maf family protein specifically in lymphoid cells (e.g., T cells or B cells). In one embodiment, the lymphoid cells are T cells. T cell specific regulatory elements are known in the art, such as the promoter regulatory region of T cell receptor genes (see e.g., Winoto and Baltimore (1989) *EMBO J.* 8:729–733; Leiden, J. M. (1994) *Annu. Rev. Immunol.* 11:539–570; Hettman, T. and Cohen, A. (1994) *Mol. Immunol.* 31:315–322; Redondo, J. M. et al. (1991) *Mol. Cell. Biol.* 11:5671–5680). Other examples of T cell specific regulatory elements are those derived from the CD3 gene (see e.g., Clevers, H. et al. (1988) *Proc. Natl. Acad. Sci. USA* 85:8623–8627; Clevers, H. C. et al. (1988) *Proc. Natl. Acad. Sci. USA* 85:8156–8160; Georgopoulos, K. et al. (1988) *EMBO J.* 7:2401–2407), the CD4 gene (see e.g., Sawada, S. and Littman, D. R. (1991) *Mol. Cell. Biol.* 11:5506–5515; Salmon, P. et al. (1993) *Proc. Natl. Acad. Sci USA* 90:7739–7743; Hanna, Z. et al. (1994) *Mol. Cell. Biol.* 14:1084–1094; see also GenBank accession numbers U01066 and S68043 for human CD4 promoter sequences) and the CD2 gene (see e.g., Zhumabekov, T. et al. (1995) *J. Immunol. Methods* 185:133–140). A DNA fragment comprising one or more T cell specific regulatory elements, such as a promoter and enhancer of a T cell receptor gene, can be obtained by standard molecular biology methods, such as by PCR using oligonucleotide primers corresponding to the 5' and 3' ends of the desired region and genomic DNA from T cells as the template. Once the DNA fragment comprising T cell specific regulatory elements is obtained, it can be operatively linked to a cDNA encoding a maf protein (e.g, the two DNA fragments can be ligated together such that the regulatory elements are located 5' of the maf sequences) and introduced into vector, such as a plasmid vector, using standard molecular biology techniques.

In another embodiment, the lymphoid cells are B cells (i.e., within the recombinant expression vector the nucleotide sequences encoding a maf family protein are operatively linked to regulatory sequences that direct expression of the maf family specifically in B cells). B cell specific regulatory elements are known in the art, such as the promoter regulatory region of inununoglobulin genes (see e.g., Banerji et al. (1983) *Cell* 33:729–740; Queen and Baltimore (1983) *Cell* 33:741–748). Other examples of B cell specific regulatory elements are those derived from the CD20 (B1) gene (see e.g., Thevenin, C. et al. (1993) *J. Biol. Chem.* 268:5949–5956; Rieckmann, P. et al. (1991) *J. Immunol.* 147:3994–3999), the Fc epsilon RIIa gene (see e.g., Suter, U. et al. (1989) *J. Immunol.* 143:3087–3092) and major histocompatibility class II genes (see e.g, Glimcher, L. H. and Kara, C. J. (1992) *Annu. Rev. Immunol.* 10:13–49; Benoist, C. and Mathis, D. (1990) *Annu. Rev. Immunol.* 8:681–715). A DNA fragment comprising B cell specific regulatory elements, such as a promoter and enhancer of an immunoglobulin gene, can be obtained by standard molecular biology methods, such as by PCR using oligonucleotide primers corresponding to the 5' and 3' ends of the desired region and genomic DNA from B cells as the template. Once the DNA fragment comprising B cell specific regulatory elements is obtained, it can be operatively linked to a cDNA encoding a maf protein (e.g., the two DNA fragments can be ligated together such that the regulatory elements are located 5' of the maf sequences) and introduced into vector, such as a plasmid vector, using standard molecular biology techniques.

In yet another embodiment, the invention provides recombinant expression vectors comprising a nucleotide sequence encoding a maf family protein operatively linked to regulatory sequences that direct expression of the maf family protein specifically in hematopoietic stem cells. Hematopoietic stem cell specific regulatory elements are known in the art. Preferably regulatory elements derived from the CD34 gene are used (see e.g., Satterthwaite, A. B. et al. (1992) *Genomics* 12:788–794; Burn, T. C. et al. (1992) *Blood* 80:3051–3059).

Another aspect of the invention pertains to recombinant host cells that express a maf family protein. Such host cells can be used to produce a Th2-associated cytokine (e.g., IL-4). Such host cells also can be administered to a subject to produce a Th2-associated cytokine in the subject as a means to manipulate Th1:Th2 ratios in the subject. The terms "host cell" and "recombinant host cell" are used interchangeably herein to refer to a cell into which a recombinant expression vector has been introduced. It is understood that such terms refer not only to the particular subject cell but to the progeny of such a cell. Because certain modifications may occur in succeeding generations due to either mutation or environmental influences, such progeny may not, in fact, be identical to the parent cell, but as long as these progeny cells retain the recombinant expression vector, these progeny are still intended to be included within the scope of the term "host cell" as used herein.

In one embodiment, the invention provides a host lymphoic cell into which a recombinant expression vector encoding a maf family protein has been introduced. The host lymphoid cell can be a T cell or a B cell. A host T cell of the invention can be, for example a T cell clone that is cultured in vitro (such as those described in the Examples) or, alternatively, a normal T cell that is isolated from a subject (e.g., a peripheral blood T cell or a splenic T cell). Standard methods for preparing and culturing T cell clones in vitro, or isolating T cells (e.g., from peripheral blood) are known in the art, for example through the use of mAbs that bind T cell specific cell surface markers (e.g., CD3) or surface markers for specific subsets of T cells (e.g., CD4 or CD8). The recombinant expression vector can be introduced into the T cell by one of a variety of known transfection methods for introducing DNA into mammalian cells, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual,* 2nd Edition, Cold Spring Harbor Laboratory press (1989)), and other laboratory manuals.

In another embodiment, the host lymphoid cell of the invention is a host B cell into which a recombinant expression vector encoding a maf family protein has been introduced. The B cell can be, for example a B lymphoma cell that is cultured in vitro (such as M12 cells as described in the Examples) or, alternatively, a normal B cell that is isolated from a subject (e.g., a peripheral blood B cell or a splenic B cell). Various B lymphoma cell lines are available in the art and standard methods for culturing such cells in vitro are known. Additionally, standard methods for isolating normal B cells (e.g., from peripheral blood) are known in the art, for example through the use of mabs that bind B cell specific cell surface markers (e.g., membrane immunoglobulin, B7-1, CD20 ). The recombinant expression vector can be introduced into the B cell by standard methods, as described above for T cells.

In yet another embodiment, the invention provides a host hematopoietic stem cell into which a recombinant expression vector encoding a maf family protein has been introduced. Hematopoietic stem cells can be isolated from a subject (e.g., from peripheral blood or bone marrow of the subject) using standard methods known in the art for isolating such stem cells, for example through the use of mAbs that bind hematopoietic stem cell specific cell surface markers, preferably CD34 (further descriptions of isolation of stem cells, see e.g., Wagner, J. E. et al. (1995) *Blood* 86:512–523; Murray, L. et al. (1995) *Blood* 85:368–378; Bernardi, A. C. et al. (1995) *Science* 267:104–108; Bernstein, I.D. et al. (1994) *Blood Cells* 20:15–24, Angelini, A. et al. (1993) *Int. J. Artif. Organs* 16 Suppl. 5:13–18; Kato, K. and Radburch, A. (1993) *Cytometry* 14:384–392; Lebkowski, J. S. et al. (1992) *Transplantation* 53:1011–1019; Lebkowski, J. et al. (1993) *J. Hematother.* 2:339–342). The recombinant expression vector can be introduced into the hematopoietic stem cell by standard methods, as described above for T cells.

V. Screening Assays

Another aspect of the invention pertains to screening assays for identifying compounds that modulate the activity of a transcription factor that regulates expression of a Th2-associated cytokine gene. In various embodiments, these screening assays can identify, for example, compounds that modulate the expression or functional activity of the transcription factor, proteins that interact with the transcription factor, as well as compounds that modulate these protein-protein interactions, and compounds that modulate the interaction of the transcription factor with a MARE within a Th2-associated cytokine gene.

In a preferred embodiment, the invention provides a method comprising:

a) preparing an indicator cell, wherein said indicator cell contains:
   i) a recombinant expression vector encoding a transcription factor that regulates expression of a Th2-associated cytokine gene; and
   ii) a vector comprising regulatory sequences of the Th2-associated cytokine gene operatively linked a reporter gene;
b) contacting the indicator cell with a test compound;
c) determining the level of expression of the reporter gene in the indicator cell in the presence of the test compound;
d) comparing the level of expression of the reporter gene in the indicator cell in the presence of the test compound with the level of expression of the reporter gene in the indicator cell in the absence of the test compound; and
e) identifying a compound that modulates the activity of a transcription factor that regulates expression of a Th2-associated cytokine gene.

Preferably, the transcription factor is a member of the maf family and most preferably a c-Maf protein. Recombinant expression vectors that can be used for expression of a c-Maf protein in an indicator cell are known in the art (see discussions above and also the Examples). In one embodiment, within the expression vector the c-Maf coding sequences are operatively linked to regulatory sequences that allow for constitutive expression of c-Maf in the indicator cell (e.g., viral regulatory sequences, such as a cytomegalovirus promoter/enhancer, can be used). Use of a recombinant expression vector that allows for constitutive expression of c-Maf in the indicator cell is preferred for identification of compounds that enhance or inhibit the activity of c-Maf. In an alternative embodiment, within the expression vector the c-Maf coding sequences are operatively linked to regulatory sequences of the c-mafgene (ie., the promoter regulatory region derived from the endogenous c-maf gene). Use of a recombinant expression vector in which c-Maf protein expression is controlled by c-maf regulatory sequences is preferred for identification of compounds that enhance or inhibit the transcriptional expression of c-Maf.

Preferably, the Th2-associated cytokine is interleukin-4. It has previously shown that Th2-specific, inducible IL-4 expression can be directed by as little as 157 bp of the proximal IL-4 promoter in Th2 cells (Hodge, M. et al. (1995) *J. Immunol.* 154:6397–6405). Accordingly, in one embodiment, the method utilizes a reporter gene construct containing this region of the proximal IL-4 promoter, most preferably nucleotides −157 to +58 (relative to the start site of transcription at +1) of the IL-4 promoter. Alternatively, stronger reporter gene expression can be achieved using a longer portion of the IL-4 upstream regulatory region, such as about 3 kb of upstream regulatory sequences. Suitable reporter gene constructs are described in Todd, M. et al. (1993) *J. Exp. Med.* 177:1663–1674. See also the Examples for descriptions of IL-4 reporter gene constructs.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which does not normally express c-Maf, such as a B cell (e.g., the M12 B lymphoma cell line) or a Th1cell clone (e.g., AE7 cells). Nonlymphoid cell lines can also be used as indicator cells, such as the HepG2 hepatoma cell line.

In one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of the transcription factor. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of the transcription factor.

Alternative to the use of a reporter gene construct, compounds that modulate the expression or activity of c-Maf can be identified by using other "read-outs." For example, an indicator cell can be transfected with a c-Maf expression vector, incubated in the presence and in the absence of a test compound, and Th2-associated cytokine production can be assessed by detecting cytokine mRNA (e.g., IL-4 mRNA) in the indicator cell or cytokine secretion (i.e., IL-4 secretion) into the culture supernatant. Standard methods for detecting cytokine mRNA, such as reverse transcription-polymerase chain reaction (RT-PCR) are known in the art. Standard methods for detecting cytokine protein in culture supernatants, such as enzyme linked immunosorbent assays (ELISA) are also known in the art. For further descriptions of methods for detecting cytokine mRNA and/or protein, see also the Examples.

In another embodiment, the invention provides a screening assay for identifying proteins in Th2 cells that interact with c-Maf. These assays can be designed based on the two-hybrid assay system (also referred to as an interaction trap assay) known in the art (see e.g., Field (1993) U.S. Pat. No. 5,283,173; Zervos et al. (1993) *Cell* 72:223–232; Madura et al. (1993) *J. Biol. Chem.* 268:12046–12054; Bartel et al. (1993) *Biotechniques* 14:920–924; and Iwabuchi et al. (1993) *Oncogene* 8:1693–1696). The two-hybrid assay is generally used for identifying proteins that interact with a particular target protein. The assay employs gene fusions to identify proteins capable of interacting to reconstitute a functional transcriptional activator. The transcriptional activator consists of a DNA-binding domain and a transcriptional activation domain, wherein both domains are required to activate transcription of genes downstream from a target sequence (such as an upstream activator sequence (UAS) for GAL4). DNA sequences encoding a target "bait" protein are fused to either of these domains and a library of DNA sequences is fused to the other domain. "Fish" fusion proteins (generated from the fusion library) capable of binding to the target-fusion protein (e.g. a target GAL4-fusion "bait") will generally bring the two domains (DNA-binding domain and transcriptional activation domain) into close enough proximity to activate the transcription of a reporter gene inserted downstream from the target sequence. Thus, the "fish" proteins can be identified by their ability to reconstitute a functional transcriptional activator (e.g., a functional GAL4 transactivator).

This general two-hybrid system can be applied to the identification of proteins in Th2 cells that interact with c-Maf by construction of a target c-Maf fusion protein (e.g., a c-Maf/GAL4 binding domain fusion as the "bait") and a cDNA library of "fish" fusion proteins (e.g., a cDNA/GAL4 activation domain library), wherein the cDNA library is prepared from mRNA of Th2 cells, and introducing these constructs into a host cell that also contains a reporter gene construct linked to a regulatory sequence responsive to c-Maf (e.g., a MARE sequence, for example a region of the IL-4 promoter, as discussed above). cDNAs encoding proteins from Th2 cells that interact with c-Maf can be identified based upon transactivation of the reporter gene construct. Accordingly, the invention provides a method for identifying a protein in a Th2 cell that interacts with c-Maf comprising:

a) providing a two hybrid assay including a host cell which contains
   i) a reporter gene operably linked to a transcriptional regulatory sequence;
   ii) a first chimeric gene which encodes a first fusion protein, said first fusion protein including c-Maf;
   iii) a library of second chimeric genes which encodes second fusion proteins, the second fusion proteins including proteins derived from Th2 cells;
   wherein expression of the reporter gene is sensitive to interactions between the first fusion protein, the second fusion protein and the transcriptional regulatory sequence;
b) determining the level of expression of the reporter gene in the host cell; and
c) identifying a protein in a Th2 cell that interacts with c-Maf.

Alternatively, a "single-hybrid" assay, such as that described in Sieweke, M. H. et al. (1996) *Cell* 85:49–60, can be used to identify proteins from Th2 cells that interact with c-Maf. This assay is a modification of the two-hybrid system discussed above. In this system, the "bait" is a transcription factor from which the transactivation domain has been removed (e.g., c-Maf from which the amino-terminal transactivation domain has been removed) and the "fish" is a non-fusion cDNA library (e.g., a cDNA library prepared from Th2 cells). These constructs are introduced into host cells (e.g., yeast cells) that also contains a reporter gene construct linked to a regulatory sequence responsive to the transcription factor (e.g., a MARE sequence, for example a region of the IL-4 promoter, responsive to c-Maf). cDNAs encoding proteins from Th2 cells that interact with c-Maf can be identified based upon transactivation of the reporter gene construct.

In yet another embodiment, the invention provides a screening assay for identifying compounds that modulate the interaction of c-Maf with a MARE in an IL-4 gene regulatory region. Assays are known in the art that detect the interaction of a DNA binding protein with a target DNA sequence (e.g., electrophoretic mobility shift assays, DNAse I footprinting assays and the like; for further descriptions see the Examples). By performing such assays in the presence and absence of test compounds, these assays can be used to identify compounds that modulate (e.g., inhibit or enhance) the interaction of the DNA binding protein with its target DNA sequence. Accordingly, the invention provides a method for identifying a compound that modulates the interaction of a c-Maf protein with a maf response element (MARE) of an IL-4 gene regulatory region, comprising:

a) providing a c-Maf protein and a DNA fragment comprising a MARE of an IL-4 gene regulatory region;
b) incubating the c-Maf protein and DNA fragment in the presence of a test compound;
c) determining the amount of binding of the c-Maf protein to the DNA fragment in the presence of the test compound;
d) comparing the amount of binding of the c-Maf protein to the DNA fragment in the presence of the test compound with the amount of binding of the c-Maf protein to the DNA fragment in the absence of the test compound; and
e) identifying a compound that modulates the interaction of a c-Maf protein with a MARE of an IL-4 gene regulatory region.

In one embodiment, the amount of binding of the c-Maf protein to the DNA fragment in the presence of the test compound is greater than the amount of binding of the c-Maf protein to the DNA fragment in the absence of the test compound, in which case the test compound is identified as a compound that enhances binding of c-Maf to the MARE. In another embodiment, the amount of binding of the c-Maf protein to the DNA fragment in the presence of the test compound is less than the amount of binding of the c-Maf protein to the DNA fragment in the absence of the test compound, in which case the test compound is identified as a compound that inhibits binding of c-Maf to the MARE.

This invention is further illustrated by the following examples which should not be construed as limiting. The contents of all references, patents and published patent applications cited throughout this application are hereby incorporated by reference. Nucleotide and amino acid sequences deposited in public databases as referred to herein are also hereby incorporated by reference.

EXAMPLE 1

Cytokine Specificity is Due to a Positive Transacting Factor and Not to a Repressor Tissue specificity can be achieved through the action of repressor or silencer proteins. Thus it was possible that the IL-2 and IL-4 genes were actively repressed in Th2 and Th1 cells respectively. To test for the existence of repressor proteins, somatic cell fusions were performed between a Th1 (D 1.1) and a Th2 (D10) clone of differing MHC Class I haplotypes. The Th1 clone D1.1 ($K^d$) and the Th2 clone D10 ($K^k$) were fused according to the "suspension cell fusion" procedure (Lane, R. D. et al. (1986) *Methods Enzymol.* 121:183–192). After fusion, the cells were allowed to recover for 8 hours and then double-stained using PE-conjugated anti-$K^k$ and FITC-conjugated anti-$K^d$ antibodies (Pharmingen, La Jolla, Calif.). Cells were then sorted on the basis of size to distinguish unfused cells from hetero and homokaryons and by fluorescence to identify single-positive and double-positive cells. As indicated in the schematic of this approach shown in FIG. 1A, three populations were sorted for: large PE-positive cells (D1.1×D1.1), large FITC-positive cells (D10×D10), and large PE and FITC positive cells (D1.1×D10). Cells expressing both MHC class I $K^b$ and $K^k$ markers were heterokaryons while cells expressing only $K^b$ or $K^k$ represented homokaryons and served as controls.

The three populations were then stimulated in culture with antibodies to CD3 to activate cytokine gene expression and RNA prepared for RT-PCR and Northern blot analysis. Approximately 5×10$^5$ cells were obtained for each population. Routinely, 5–10% of the cells had undergone fusion. Each of these three populations was then split in half, one half transferred to pre-rinsed anti-CD3 coated plates, the remaining half to uncoated plates. After four hours, the cells were harvested, and poly(A+) RNA isolated using the Micro-FastTrack™ kit (Stratagene, La Jolla, Calif.). cDNA was made using the SuperScript kit (Gibco/BRL, Bethesda, Md.), and used for PCR analysis using commercially available primers specific for murine IL-2, IL-4 and β-actin according to the manufacturer's instructions (Stratagene, La Jolla, Calif.). PCR reactions included 0.5 $\mu$Ci α-$^{32}$P-dCTP (3000 Ci/mmol, NEN Dupont). PCR products were ethanol precipitated, separated by nondenaturing PAGE and dried and visualized by autoradiography.

Figure 1B:
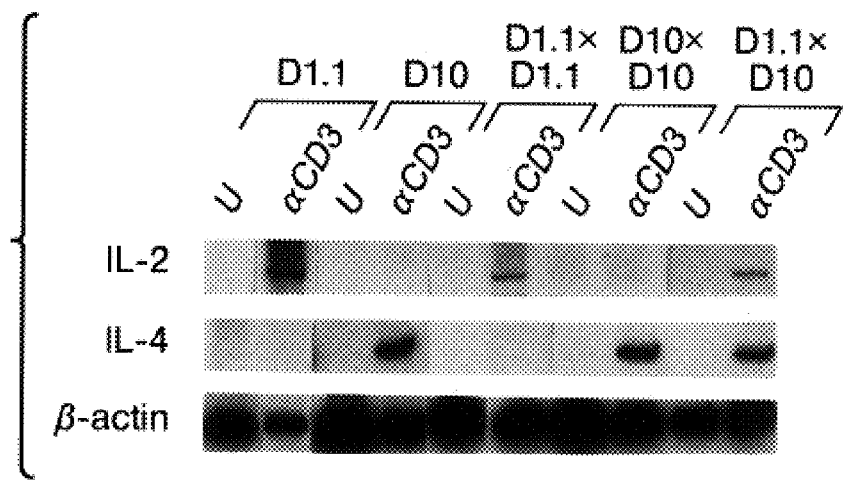
FIG. 1B is a reverse transcriptase-polymerase chain reaction (RT-PCR) analysis of Il-2 and IL-4 cytokine, and control β-actin, mRNA expressed by an unfused Th1 clone (D1.1), an unfused Th2 clone (D10), Th1 and Th2 homokaryons and Th1–Th2 heterokaryons.

The results of the RT-PCT analysis of cytokine mRNA expression are shown in FIG. 1B. The Th1 and Th2 clones and the Th homokaryons transcribed only IL-2 (Th1) or IL-4 (Th2) respectively, while the Th1/Th2 heterokaryons produced both cytokines. In contrast, the existence of repressor protein(s) should have resulted in the extinction of both cytokines in the heterokaryons. From these experiments, it was concluded that cytokine specificity in Th1 vs. Th2 cells was mediated by Th-specific positive transacting factors rather than by selective silencer proteins.

EXAMPLE 2

Figure 2A:
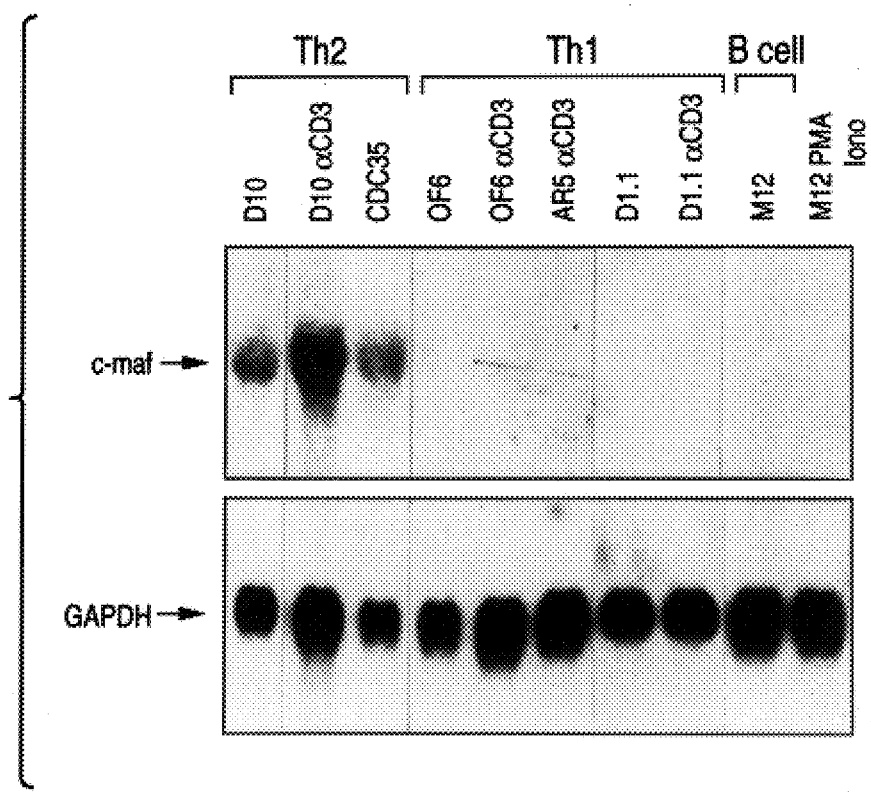
FIG. 2A is a Northern blot analysis depicting expression of an isolated cDNA clone in Th1 cells, Th2 cells or B lymphoma cells. A control probe specific for GAPDH was used to show equal loading of RNA.

Isolation of a Th2-Specific c-maf Gene from a cDNA Library Prepared from an Anti-CD3 Activated Th2 Clone In the course of screening a cDNA library prepared from an anti-CD3 activated Th2 clone, D10, for NF-AT-interacting proteins by the yeast two-hybrid system (for descriptions of this system, see e.g., Field U.S. Pat. No. 5,283,173; Zervos et al. (1993) *Cell* 72:223–232; Madura et al. (1993) *J. Biol. Chem.* 268:12046–12054; Bartel et al. (1993) *Biotechniques* 14:920–924; and Iwabuchi et al. (1993) *Oncogene* 8:1693–1696), multiple cDNAs were isolated, all of which were extremely weak interactors. All cDNAs obtained in this screen were next evaluated for Th-specific expression by Northern blot analysis using a panel of Th1 and Th2 clones. One such cDNA, which was repeatedly isolated (60 of 140) detected transcripts only in RNA prepared from Th2 clones (D10, CDC35) and not from either Th1 clones (AR5, OS6, D1) or from a B cell lymphoma, M12, as illustrated in the Northern blot analysis depicted in FIG. 2A. Further, the levels of transcripts detected in D10 Th2 cells were substantially increased upon activation by ligation of the T cell receptor with anti-CD3 antibody. No induction of the transcript detected by this cDNA clone occurred in Th1 clones upon anti-CD3 treatment. A control probe, GAPDH, demonstrated approximately equal loading of RNA in all lanes. Thus, the expression of this cDNA clone in the lymphoid lineage appeared to be Th2-specific and sensitive to signals transmitted through the T cell receptor. For these Northern blots, total RNA was prepared by using Trizol (GIBCO/BRL) according to manufacturer's instructions. 10 $\mu$g of total RNA from each sample was fractionated on a formaldehyde agarose gel and transferred to a nylon membrane. A 300 bp DraI fragment derived from the 3' untranslated region of the isolated clone was labeled with α-$^{32}$P-dCTP using Random Primed DNA Labeling Kit (Boehringer Mannheim, Indianapolis, Ind.). Hybridization was performed using QuikHyb (Stratagene, La Jolla, Calif.) according to manufacturer's instructions.

To determine whether the expression of this gene was tissue-specific and regulated during the course of normal Th cell development, the following experiment was performed.

Naive spleen cells (Th precursor (Thp) cells) were driven along a Th1 or Th2 pathway by treatment with anti-CD3 in the presence of cytokines and anti-cytokine antibodies (IFNγ and anti-IL-4 for Th1, IL-4 and anti-IFNg for Th2). Splenic cell suspensions were prepared from 6–8 week-old Balb/c mice, cultured in RPMI 1640 supplemented with 10% FCS at a density of 10$^6$ cells/ml, and stimulated with plate bound anti-CD3 antibody in the presence of 5 $\mu$g/ml of anti-IL4 antibody (11B11) for the Th1 lineage, or 5 $\mu$g/ml of anti-IFNγ antibody (XMG-1) for the Th2 lineage. 24 hours after stimulation, 50 U/ml IL2 was added to all cultures, and 500 U/ml IL4 (Genzyme) was added to Th2 cultures. 7 days after the primary stimulation, all cells were harvested, washed and restimulated with plate bound anti-CD3 antibody. Northern blot analysis of differentiating cells harvested at various time points after stimulation in a primary (day 0–8) and secondary (0–20 hours) response was performed, using the methodology described above, and identification of differentiating Thp cells as Th1 or Th2 was determined by analyzing culture supernatants by ELISA for IL-10 and IFNγ. ELISA for cytokine quantitation was performed as follows. All anti-cytokine antibodies were purchased from Pharmingen. ELISA was performed according to Pharmingen's instructions with the exception that Avidin-Alkaline Phosphatase (Sigma) at 1:500 dilution in PBS/BSA was used in place of avidin-peroxidase. P-nitrophenyl phosphate (GIBCO BRL) at 4 mg/ml in substrate buffer (10% diethanolamine, 0.5 mM MgCl$_2$, 0.02% sodium azide, pH 9.8) was used as substrate.

Figure 2B:
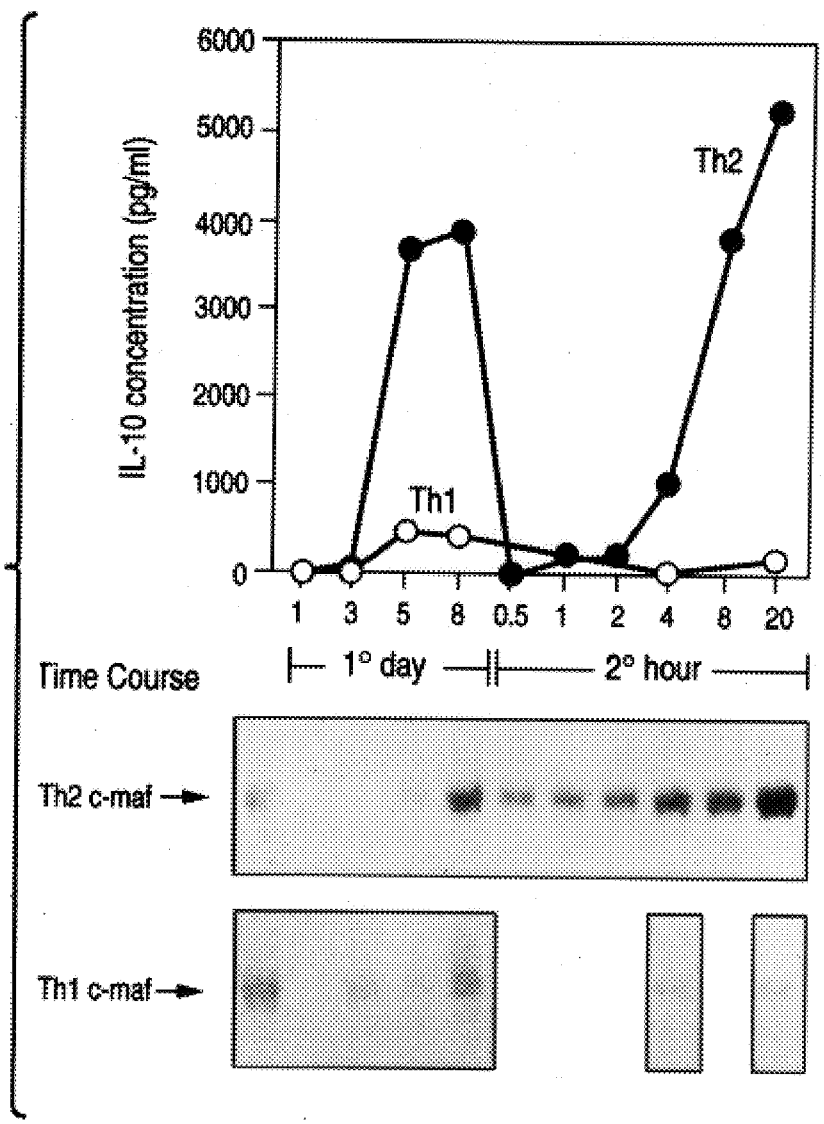
FIG. 2B is a Northern blot analysis depicting upregulated expression of the isolated cDNA clone during in vitro differentiation of normal naive spleen cells into Th2 cells. Total RNA was isolated from cells harvested at the indicated time points. Culture supernatant at the appropriate dilution was measured for cytokine (IL-10) production by ELISA to determine differentiation into the Th1 or Th2 lineage.

In two independent experiments, representative results of which are shown in FIG. 2B, this analysis revealed low level or undetectable expression of this cDNA in naive spleen cells at baseline at day 0. In cultures differentiating along a Th2 pathway, substantial induction of transcripts occurred by day 8 in a primary stimulation and by 20 hr in a secondary stimulation. In contrast, no induction occurred in cells being driven along a Th1 pathway. A control probe (GAPDH) showed approximately equal loading of RNA in all lanes. The low level of transcripts present in cells being driven along a Th1 pathway likely reflects the presence of residual Th2 cells since complete skewing does not occur in this in vitro differentiation system.

Together, these experiments revealed that the isolated cDNA is selectively expressed in Th2 clones, where it is induced upon T cell activation, and that it is absent from Th1 clones and a B lymphoma. Further, this gene is induced in normal Thp when they are driven towards the Th2 lineage, but is not induced during Th1 development.

The cDNA obtained from the yeast two-hybrid screen was used as a probe to isolate a full-length cDNA from a D10 Th2 cell cDNA library by standard hybridization methods. A 4.3 kb cDNA clone was isolated from the Th2 cell library and sequenced by standard methods. Sequence analysis revealed that this Th2-specific gene corresponded in sequence to the c-maf proto-oncogene.

EXAMPLE 3

Ectopic Expression of c-Maf in Th1 and B Cells Results in Activation of the IL-4 Promoter The identification of the isolated cDNA described in Example 2 as a member of the AP-1/CREB/ATF gene family, together with its selective expression in Th2 cells raised the possibility that c-Maf controlled the tissue-specific transcription of the IL-4 gene. Additionally, the presence of transcripts encoding c-maf correlated well with IL-4 expression in Th2 cells and in three of four transformed mast cell lines examined. To test whether c-Maf could transactivate the IL-4 promoter, cotransfection experiments were performed.

Th1 clones and the B lymphoma M12.4.C3 (M12) neither express c-maf nor transcribe the IL-4 gene. If c-Maf is the transcription factor critical for controlling IL-4 gene expression, then forced expression in these cells should permit IL-4 gene expression. To test this, the full-length (4.3 kb) c-maf cDNA clone was inserted into the SalI site of the pMex-NeoI mammalian expression vector, which utilizes the CMV enhancer to drive expression of the inserted sequence. The c-Maf expression vector was then cotransfected with an IL-4 promoter reporter construct into the Th1 clone AE7 and the B lymphoma M12. The generation of the wild type IL4 CAT reporter construct, containing an IL4 promoter fragment from −157 to +68 operatively linked to a chloramphenicol acetyltransferase gene is described in Hodge, M. et al. (1995) J. Immunol. 154:6397–6405. The Th1clone was cultured in RPMI 1640 supplemented with 10% FCS and 10% Con-A stimulated rat splenocyte supernatant, and maintained by bi-weekly stimulation with appropriate antigen and APCs. M12 cells were cultured in RPMI 1640 supplemented with 10% FCS.

The Th1 clone AE7 or M12 B lymphoma cells were transiently transfected by preincubating 0.4 ml of cells, containing $2\times10^7$ cells/ml AE7 or $3\times10^6$ cells/ml M12 cells in serum-free RPMI 1640 with 20 µg (AE7) or 5 µg (M 12) of each plasmid for 10 minutes at room temperature. The samples were then electroporated using a BIO-RAD Gene Pulser (BIO-RAD, Richmond, Calif.) set at 975 µF, 280 V, and immediately placed on ice for 10 minutes. The transfected cells were allowed to recover overnight in complete media and stimulated with plate bound anti-CD3 antibody ({Pharmingen, San Diego, Calif.} 1 µg/ml in IXPBS overnight at 4° C.) or with 50 ng/ml PMA (Sigma, St. Louis, Mo.) and 1 µM Ionomycin (Calbiochem Corp., La Jolla, Calif.). for 24 hours. Cell lysate was prepared by freeze-thaw lysis in 0.25M Tris-Cl, pH 7.8. Equal amounts of protein (between 5–20 µg) were used for CAT assays. CAT assays were performed as described in Todd, M. et al. (1993) J. Exp. Med. 177:1663–1674.

Figure 3A:
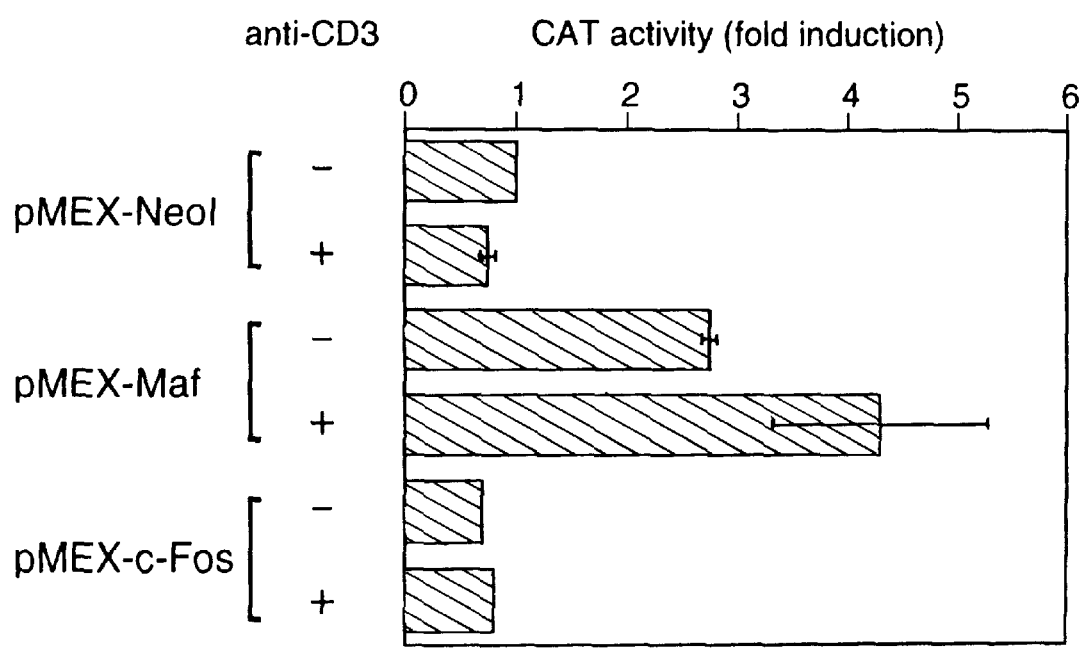
FIG. 3A is a bar graph depicting transactivation of the IL-4 promoter by c-Maf in a Th1 clone (AE7). AE7 cells were cotransfected with a wild-type IL-4 CAT reporter construct and either a control plasmid (pMEX-NeoI), a c-Maf expression plasmid (pMEX-Maf) or a c-Fos expression plasmid (pMEX-c-Fos). Half of each sample was stimulated 24 hours after transfection with antibodies to CD3. All samples were harvested 48 hours after transfection and relative CAT activities were determined.
Figure 3B:
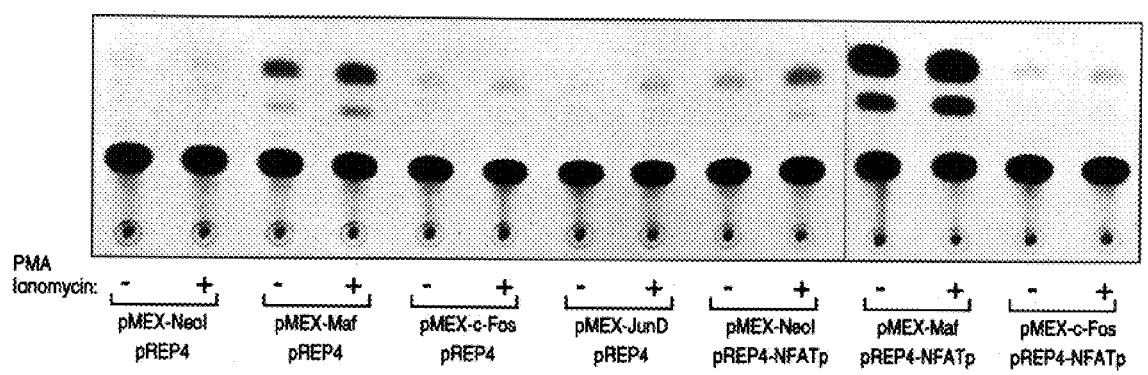
FIG. 3B is a photograph of a thin layer chromotography plate depicting the relative CAT activity in M12 B lymphoma cells cotransfected with a wild-type IL-4 CAT reporter construct and either two control plasmids (pMEX-NeoI and pREP4), a c-Maf expression plasmid and a control plasmid (pMEX-Maf and pREP4), a c-Fos expression plasmid and a control plasmid (pMEX-c-Fos and pREP4), a c-Jun expression plasmid and a control plasmid (pMEX-c-Jun and pREP4), a control plasmid and an NF-ATp expression plasmid (PMEX-NeoI and pREP-NFATp), a c-Maf expression plasmid and an NFATp expression plasmid (pMEX-Maf and pREP-NFATp) or a c-Fos expression plasmid and an NF-ATp expression plasmid (pMEX-c-Fos and pREP-NFATp). Half of each sample was stimulated 24 hours after transfection with PMA and ionomycin. All samples were harvested 48 hours after transfection and relative CAT activities were determined.

It has previously shown that Th2-specific, inducible IL-4 expression can be directed by as little as 157 bp of the proximal IL-4 promoter in Th2 cells (Hodge, M. et al. (1995) J. Immunol. 154:6397–6405). In cotransfection experiments, the results of which are summarized in FIG. 3A, it is demonstrated that ectopic expression of c-Maf in the Th1 clone AE7 results in substantial activity of the IL-4 promoter reporter after stimulation through the T cell receptor. The fold induction observed was approximately 5 fold over that observed with the control empty vector alone. Although expression of a reporter construct containing proximal (−157 to +58) IL-4 promoter sequences in the subclone of AE7 cells utilized here has not been previously observed, it has been demonstrated that small amounts of IL-4 mRNA can be detected by RT-PCR in other subclones of AE7. To more rigorously test the ability of c-Maf to transactivate the IL-4 promoter in a non-IL-4 producing cell, the same experiment was performed in the B lymphoma cell line, M12. Normal B cells and B lymphoma cells do not produce IL-4. Representative results of the cotransfection experiments are depicted in FIG. 3B and a summary of three independent experiments is shown below in Table 1.

TABLE 1

| Plasmids | PMA/iono. | CAT Activity (fold induction) | | |
| --- | --- | --- | --- | --- |
| | | Exp. I* | Exp. II | Exp. III |
| pMEX-NeoI/pREP4 | − | 1 | 1 | 1 |
| | + | 7.6 | 1 | 1.4 |
| pMEX-Maf/pREP4 | − | 95 | 5 | 18.6 |
| | + | 186 | 7 | 37 |
| pMEX-c-Fos/pREP4 | − | 2.7 | 1 | 0.8 |
| | + | 7.6 | 1.2 | 1 |
| pMEX-JunD/pREP4 | − | ND** | 0.9 | 0.5 |
| | + | ND | 1.4 | 1.9 |
| pMEX-NeoI/pREP4-NFATp | − | 14.2 | 1.6 | 0.3 |
| | + | 41.2 | 3.5 | 0.3 |
| pMEX-Maf/pREP4-NFATp | − | 136 | 54 | 26.3 |
| | + | 138 | 100 | 54.7 |
| pMEX-c-Fos/pREP4-NFATp | − | 7.4 | 1.6 | 3 |
| | + | 15.4 | 1.9 | 6.1 |

*In experiment I, 20 mg of cell lysate was incubated for 2 hours. In experiments II and III, only 5 mg of cell lysate was incubated for 1 hour in order to reveal synergy between c-Maf and NFATp
**ND = not done The results in M12 B lymphoma cells confirmed the findings in the Th1 clone. Ectopic expression of c-Maf resulted in substantial activity of the IL-4 promoter in M12 cells, either unstimulated or stimulated with PMA/Ca++ ionophore. The fold induction observed when compared to transfection of a control vector averaged approximately 50 in unstimulated M12 cells. Stimulation of M12 cells with PMA/Ca++ ionophore, which should result in translocation of NF-ATs to the nucleus and induction of other AP-1 family members (Flanagan, W. M. (1991) Nature 352:803–807; Jain, J. et al. (1993) Nature 365:352–355), increased the basal activity of the IL-4 promoter, but a marked induction in promoter activity by c-Maf was still present (average of approximately 25 fold). C-Maf did not transactivate a control reporter driven by NF-AT multimers, demonstrating the specificity of transactivation.

As a control for the specificity of c-Maf as opposed to other AP-1 family members, the c-Fos and c-Jun proteins were also overexpressed in M12 cells utilizing murine full-length cDNAs encoding c-Fos and JunD in the mammalian expression vector of pMEX-NeoI together with the IL-4 reporter plasmid. No IL-4 promoter activity could be achieved by overexpression of either of these two AP-1 family members in M12 cells. Thus, c-Maf has a unique ability to drive IL-4 gene transcription in M12 B cells.

Further, forced expression of c-Maf in the hepatoma cell line HepG2 also resulted in IL-4 promoter transactivation. These experiments demonstrate that the provision of c-Maf to c-Maf negative Th1 or B cells, or to non-lymphoid cells (e.g., a hepatoma cell line), permits the cells to transactivate the IL-4 promoter.

NF-AT proteins have been shown to be critically important in the regulation of both the IL-4 and IL-2 cytokines. NF-ATp was the first member of this family to be isolated (McCaffrey, P. G. et al. (1993) Science 262:750–754). Both AE7 and M12 cells have endogenous NF-ATp protein, but nevertheless do not transcribe IL-4. Although NF-ATp could not therefore account for selective IL-4 gene transcription, it was of interest to test whether overexpression of NF-ATp in unstimulated or stimulated M12 cells would further increase the transactivation of the IL-4 promoter by c-maf. M12 cells were cotransfected with the IL-4 reporter construct and either an NFAPp expression vector (pREP$_4$-NF-ATp, which also carries a hygromycin resistance gene) alone or the NFAPp expression vector together with the c-Maf expression vector. Overexpression of NF-ATp alone in M12 cells resulted in some modest transactivation of the IL-4 promoter. This transactivation was markedly increased by ectopic expression of c-Maf, an increase which was not just additive but was synergistic (see FIG. 3B and Table 1). In contrast, c-Fos overexpression did not further increase the modest transactivation achieved by NF-ATp. These results indicate that c-maf and NF-ATp interact to achieve maximal induction of the IL-4 promoter, the tissue-specificity being provided by c-maf.

EXAMPLE 4

Ectopic Expression of C-Maf Activates Transcription of the Endogenous IL-4 Gene in a B Lymphoma As demonstrated in Example 3, c-Maf transactivates the IL-4 promoter in transient transfection assays in Th1, B and non-lymphoid cells. To test whether expression of c-maf in non-IL-4 producing cells can activate the transcription of endogenous IL-4, the B lymphoma M12 was stably transfected with expression vectors encoding c-maf, NF-ATp or both, or junD with and without NF-ATp as a control. For stable transfection, M12 cells were transfected as described above in Example 3. The transfected cells were allowed to recover in complete media for 48 hours before the addition of Neomycin (GIBCO/BRL, Gaithersburg, Md.) and Hygromycin (Calbiochem, Corp.) at a concentration of 400 μg/ml of each antibiotic. The transfected cells were supplemented with fresh media every other day.

Figure 4:
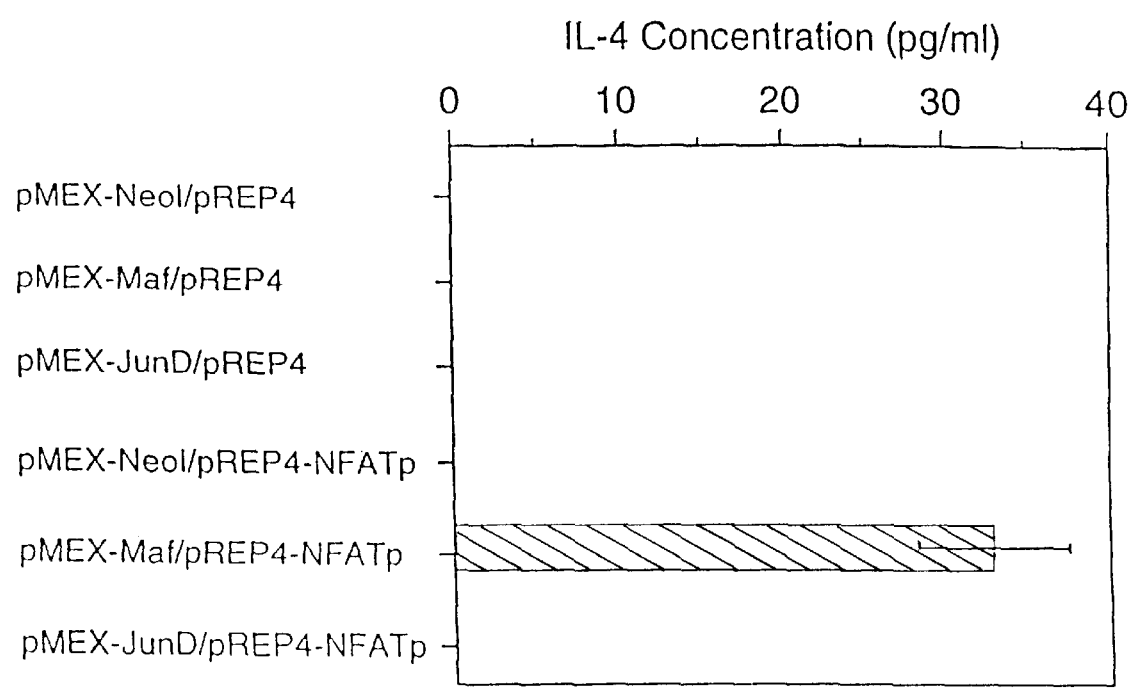
FIG. 4 is a bar graph depicting endogenous production of IL-4 in M12 cells by ectopic expression of c-Maf and NF-ATp. Cells stably transfected with the indicated control or expression plasmids were either unstimulated or stimulated with PMA and ionomycin for 24 hours. 200 μl of supernatant from each sample was subjected to ELISA for cytokine quantitation.

Stably transfected M12 cells were plated at equal density supernatants harvested 24 hours later to measure cytokines by ELISA. ELISAs were performed as described in Example 2. The results, shown in FIG. 4, demonstrate that in these experiments M12 cells transfected with c-maf, junD or NF-ATp alone did not produce measurable IL-4 by ELISA. However, M12 cells stably transfected with both c-maf and NF-ATp did produce detectable, but low level, IL-4 by ELISA. These results were confirmed by RT-PCR on RNA from these transfected cells. In contrast, these cells did not produce detectable IL-2. The requirement for both c-maf and NF-ATp is consistent with the synergistic effect of these factors in the transactivation of the IL-4 promoter noted in the transient transfection experiments in M12 cells. In contrast, transfection of jund, an AP-1 family member which can increase IL-4 expression in Th2 cells, alone or together with NF-ATp, did not result in IL-4 production. These results demonstrate the essential and selective role of c-maf in directing tissue-specific endogenous IL-4 production.

EXAMPLE 5

Figure 5A:
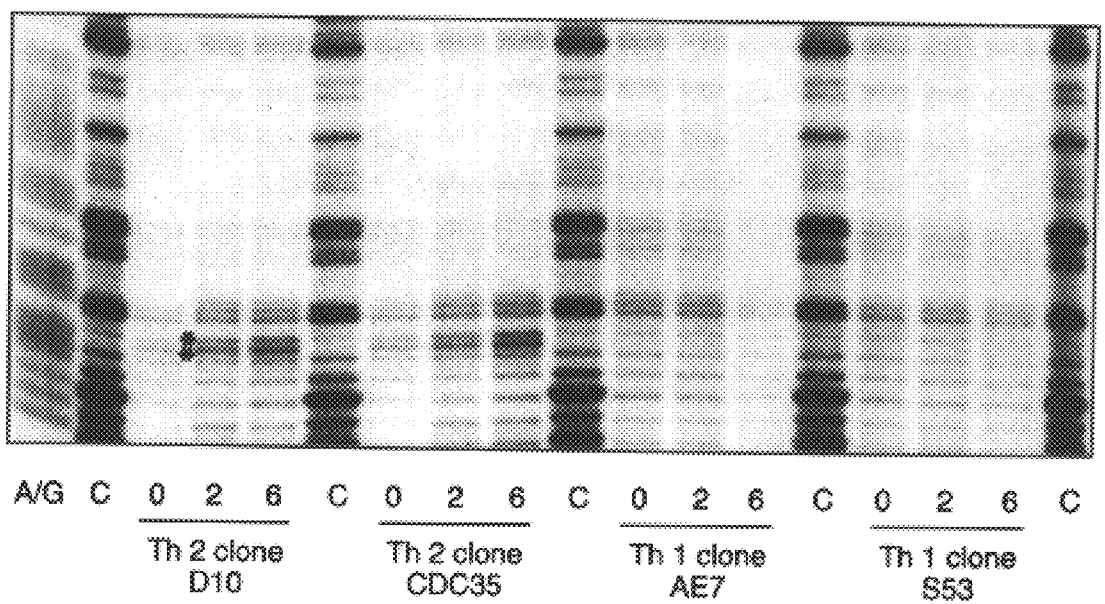
FIG. 5A is a photograph of a DNAse I footprint gel of the IL-4 promoter performed using nuclear extracts from Th2 (D10, CDC35) or Th1 (AE7, S53) clones harvested at the indicated time points after stimulation with anti-CD3 antibodies, which depicts a Th2-specific footprint immediately downstream of the putative MARE site in the IL-4 promoter. Two Th2-specific hypersensitive residues on the non-coding strand of the IL-4 promoter are indicated by *. Five lanes of a DNAse I digestion of the IL-4 promoter probe (without nuclear extract) and a Maxam-Gilbert A/G ladder were run next to the DNAse I treated samples.
Figure 5B:
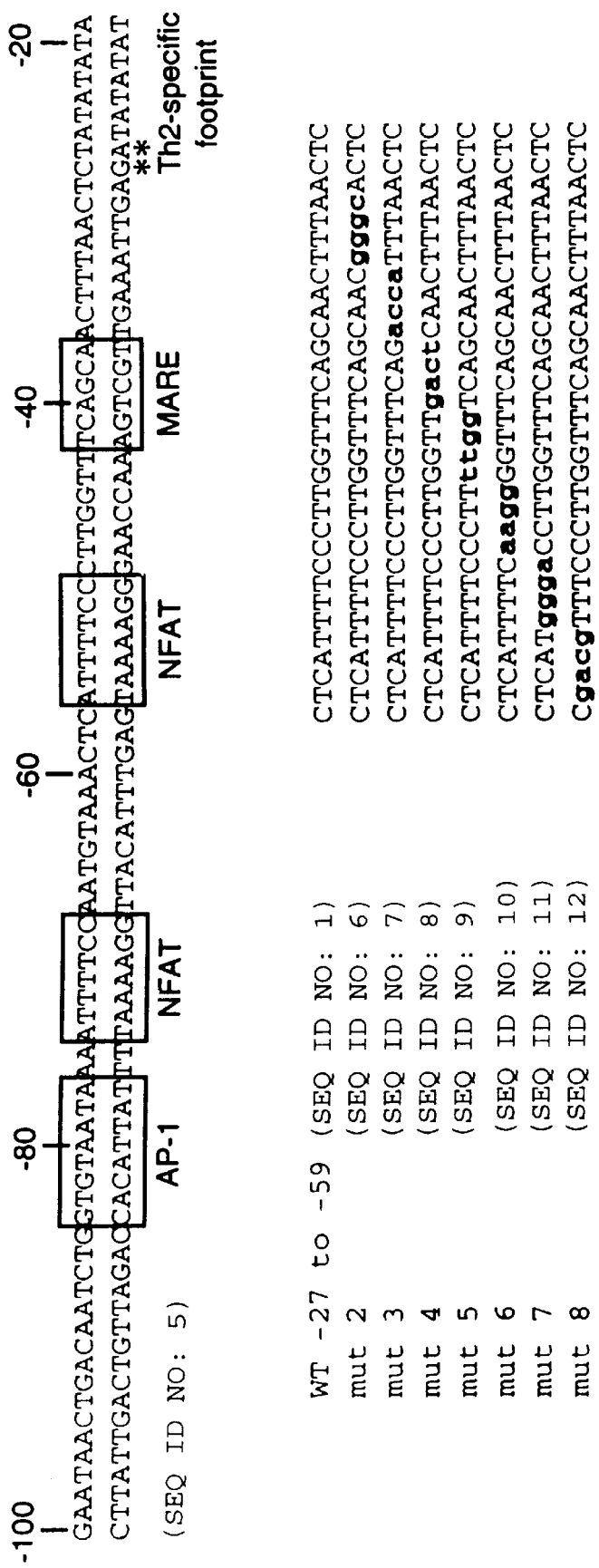
FIG. 5B is a schematic representation of the proximal regulatory region of the murine IL-4 promoter. The top portion shows the primary sequence of the murine IL-4 promoter. The numbers indicated are relative to the start site of transcription at +1. Asterisks denote the Th2-specific hypersensitive residues seen on DNAse I footprint. The bottom portion shows the sequence of the wild type (−59 to −28) oligonucleotide and the 4 bp mutants used in EMSA and the functional assays shown in FIGS. 6 and 7. Altered nucleotides are shown in lowercase bold and correspond to the numbering system shown in the top portion.

A Site in the IL-4 Promoter is Footprinted by Extracts from Th2 but not Th1 Clones The experiments described in Examples 3 and 4 demonstrated a clear functional role for c-maf in controlling tissue-specific expression of IL-4. Further, c-maf transcripts were expressed in Th2 but not Th1 cells. However, DNA-protein complexes were not detected by electrophoretic mobility shift assays (EMSA) when using nuclear extracts prepared from Th2 cells. To further examine whether a protein in Th2 nuclear extracts might bind to the MARE, or nearby sequences, the more sensitive technique of DNAseI footprinting was used. Two Th2 clones (D10, CDC35) and two Th1 clones (AE7, S53) were activated by ligation of the T cell receptor with plate-bound anti-CD3 antibody, and nuclear extracts prepared at time 0 (unstimulated), 2 hours and 6 hours later. DNAseI footprinting analysis was then performed according to standard methods using a Klenow end-labeled IL-4 promoter fragment (−157 to +68). The results are shown in FIG. 5A. Stimulated extracts from both Th1 and Th2 cells footprinted the two NF-AT sites and the AP-1 site upstream of the distal NF-AT site as described previously (Rooney, J. et al. (1995) Immunity 2:545–553), consistent with the demonstrated function of NF-AT and AP-1 proteins in regulating both the IL-2 and the IL-4 promoters (Rooney, J. et al. (1995) Immunity 2:545–553; Rooney, J. et al. (1995) Mol. Cell. Biol. 15:6299–6310). Furthermore, inspection of the autoradiograph revealed an area of hypersensitivity on the non-coding strand at residues −28 and −29 when extracts from stimulated Th2 but not stimulated Th1 cells were used. Unstimulated Th cell extracts did not footprint this region. The Th2 footprint observed was subtle, but reproducible in two experiments and is located in a site that has previously been demonstrated to be critical for IL-4 promoter activation in Th2 cells (Hodge, M. et al. (1995) J. Immunol. 154:6397–6405). A schematic summary of sites occupied in the IL-4 promoter as detected by footprint analysis is shown in FIG. 5B. These results indicate that a site in the proximal IL-4 promoter, previously shown to be functionally important, is occupied in activated Th2 but not in activated Th1 cells.

EXAMPLE 6

Recombinant c-maf Binds to a MARE Site in the IL-4 Promoter

The Th2-specific footprint does not contain a c-maf response element (MARE). However, examination of the proximal IL-4 promoter revealed a half c-maf binding site (MARE) (residues −42 to −37) immediately downstream of the proximal NF-AT site (residues −56 to −51) (shown schematically in FIG. 5B). It has previously been demonstrated that mutation of this site abolished activity of the IL-4 promoter in Th2 cells (Hodge, M. et al. (1995) J. Immunol. 154:6397–6405). To determine if c-Maf bound this site, a truncated c-Maf recombinant protein containing the b-zip domain(amino acids 171–371) was expressed from E. coli, purified on an S-Tag agarose column and used in electrophoretic mobility shift assays with radiolabeled MARE oligonucleotide.

The expression vector for recombinant c-Maf was constructed by inserting a cDNA fragment encoding a.a. residues 171 to 371 of c-Maf (disclosed in Kurschner C. and Morgan, J. I. (1995) *Mol. Cell. Biol.* 15:246–254) into the NotI site of pET29 (Novagen, Inc. Madison, Wis.). The truncated c-Maf protein was expressed using T7 polymerase in the BL21(DE3)strain. Cells were induced by the addition of 1 mM IPTG and incubated at 37° C. for 3 hours. The induced cells were lysed in 1×Bind/Wash buffer (20 mM Tris-HCI pH 7.5, 150 mM NaCl, 0.1% Triton X-100) followed by sonication. The c-Maf protein was then purified from the soluble fraction by using the S-Tag Purification Kit (Novagen) according to manufacturer's instructions. Two additional proteins, NF-ATp and c-Jun, were also used in EMSA assays. The recombinant NF-ATp, containing the Rel domain of murine NF-ATp, was expressed using an in vitro transcription/translation vector TP7-NF-ATp, which contains a cDNA fragment encoding the Rel domain of murine NF-ATp. The c-Jun expression vector, pGEM-c-Jun, was constructed by inserting a full-length cDNA of murine c-Jun into the PstI site of pGEM4. 1 µg of each plasmid DNA was transcribed from the T7 promoter and translated in rabbit reticulocyte lysate by using the TnT Coupled Transcription/ Translation Kit (Promega, Madison, Wis.).

Electrophoretic mobility shift assays (EMSA) were performed as follows. 100 mg of double-stranded oligonucleotides were end-labeled with $\gamma$-$^{32}$P-dATP (DuPont NEN Research Product, Wilmington, Del.) using T4 polynucleotide kinase (Pharmacia LKB Biotechnology, Inc., Piscataway, N.J.). The labeled ds-oligonucleotides were fractionated on 15–20% polyacrylamide gels, eluted overnight at 37° C. in 1×TE and precipitated in ethanol. Binding assays were performed at room temperature for 20 minutes using 0.5 µg of recombinant proteins or 4 µl of in vitro translated products, 500 ng poly(dI-dC), and 20,000 cpm of probe in a 15 µl volume of 20 mM HEPES (pH 7.9), 100 mM KCI, 5% glycerol, 1 mM EDTA, 5 mM DTT, 0.1% NP-40, and 0.5 mg/ml BSA. The samples were then fractionated in 4% non-denaturing polyacrylamide gel containing 0.5×TBE at room temperature. Oligonucleotides derived from the murine IL4 promoter used in EMSA were: –59 to –27: 5'-CTCATTTTCCCTTGGTTTCAGCAACTTTAACTC-3' (SEQ ID NO: 1); –79 to –60: 5'-ATAAAATTTTCCAATGTAAA-3' (SEQ ID NO: 2); and –88 to –61: 5'-TGGTGTAATAAAATTTTCCAATGTAAA-3' (SEQ ID NO: 3).
The sequence of the MARE oligonucleotide used in EMSA was: 5'-GGAATTGCTGACTCAGCATTACT-3' (SEQ ID NO: 4).
All oligonucleotides were annealed with their respective reverse-complementary strands to form double-stranded oligonucleotides.

Figure 6:
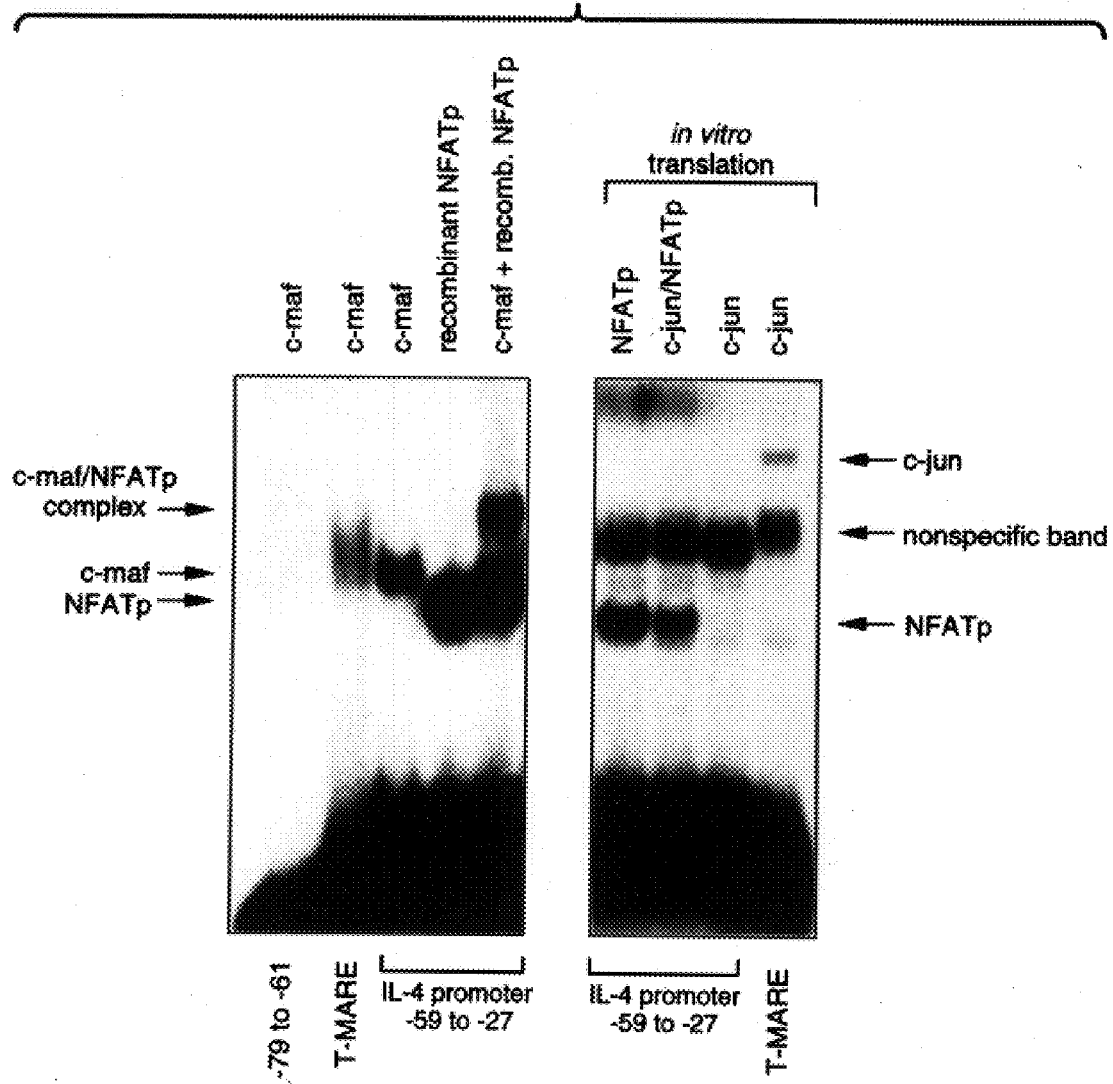
FIG. 6 is a photograph of an electrophoretic mobility shift assay (EMSA) demonstrating that c-Maf but not c-Jun binds to the proximal IL-4 promoter and forms a complex with NF-ATp. EMSA was performed using the indicated proteins and labeled double-stranded oligonucleotides.

The results of EMSA with recombinant c-Maf are shown in FIG. 6. The recombinant c-Maf protein bound well to both a consensus MARE oligonucleotide and to a 33 bp oligonucleotide containing the NF-AT site and MARE present in the IL-4 promoter. Binding was specifically competed by unlabeled homologous but not control probe. Further, c-Maf did not bind to an oligonucleotide containing only the NF-AT target sequence to which recombinant NF-ATp bound well. The ability of c-Maf to bind to the IL-4 promoter probe was specific since in vitro translated c-Jun protein did not bind to this oligonucleotide. The c-Jun protein was functional since it could bind to the consensus MARE which contains a core TRE site. These results indicate that c-Maf, but not another AP-1 family member (c-Jun), can bind to the MARE site within the proximal IL-4 promoter.

NF-AT proteins interact cooperatively with AP-1 family member proteins to form higher mobility complexes on IL-2 and IL-4 promoter DNA on EMSA (Jain, J. (1993) *Nature* 365:353–355; Rooney, J. et al. (1995) *Immunity* 2:545–553). That NF-AT proteins might interact with c-maf was suggested by the functional studies described in the previous examples. To determine if c-Maf interacted with NF-AT in the presence of DNA, recombinant NF-ATp and c-Maf proteins were used separately or together in EMSA with the 33 bp oligonucleotide containing both the NF-AT and adjacent MARE sites. The results are shown in FIG. 6. Each protein alone bound to IL-4 promoter DNA. Recombinant c-Maf plus recombinant NF-ATp protein produced these complexes and in addition formed a higher mobility complex. No higher mobility complex was observed when c-Jun and NF-ATp proteins were used, consistent with the failure of c-Jun to bind this site. These results indicate that c-Maf can specifically bind in vitro to a sequence located in the proximal IL-4 promoter, previously shown to be functionally critical in Th2 cells, and that, like other AP-1 proteins, c-Maf can interact in vitro with NF-AT proteins.

EXAMPLE 7

Figure 7A:
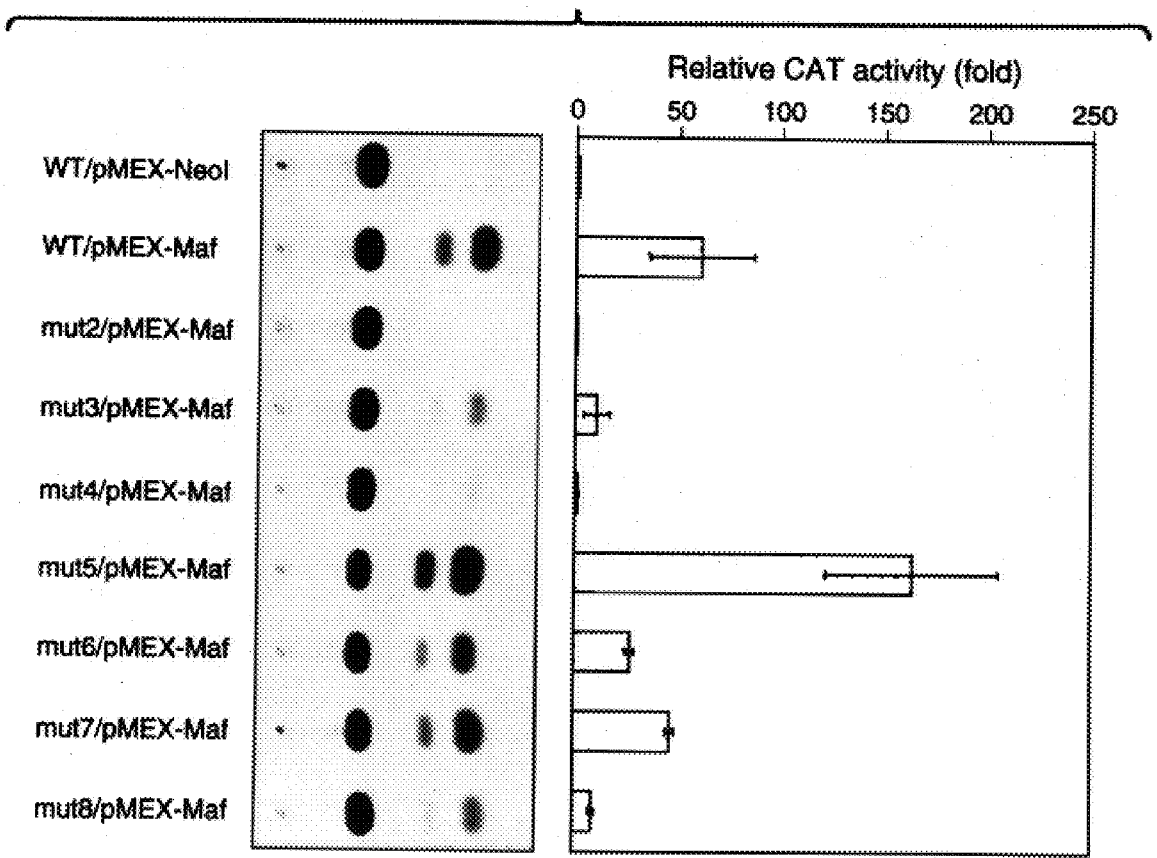
FIG. 7A is a bar graph (top) and a photograph of a thin layer chromotography plate (bottom) depicting the relative CAT activity in M12 cells co-transfected with a c-Maf expression vector and either the wild-type IL-4 CAT reporter construct or one of the 4 bp mutants shown in FIG. 5B, demonstrating that transactivation of the IL-4 promoter by c-Maf maps to the MARE and Th2-specific footprint. The average of three independent experiments and one representative experiment are shown in the top and bottom portions, respectively.
Figure 7B:
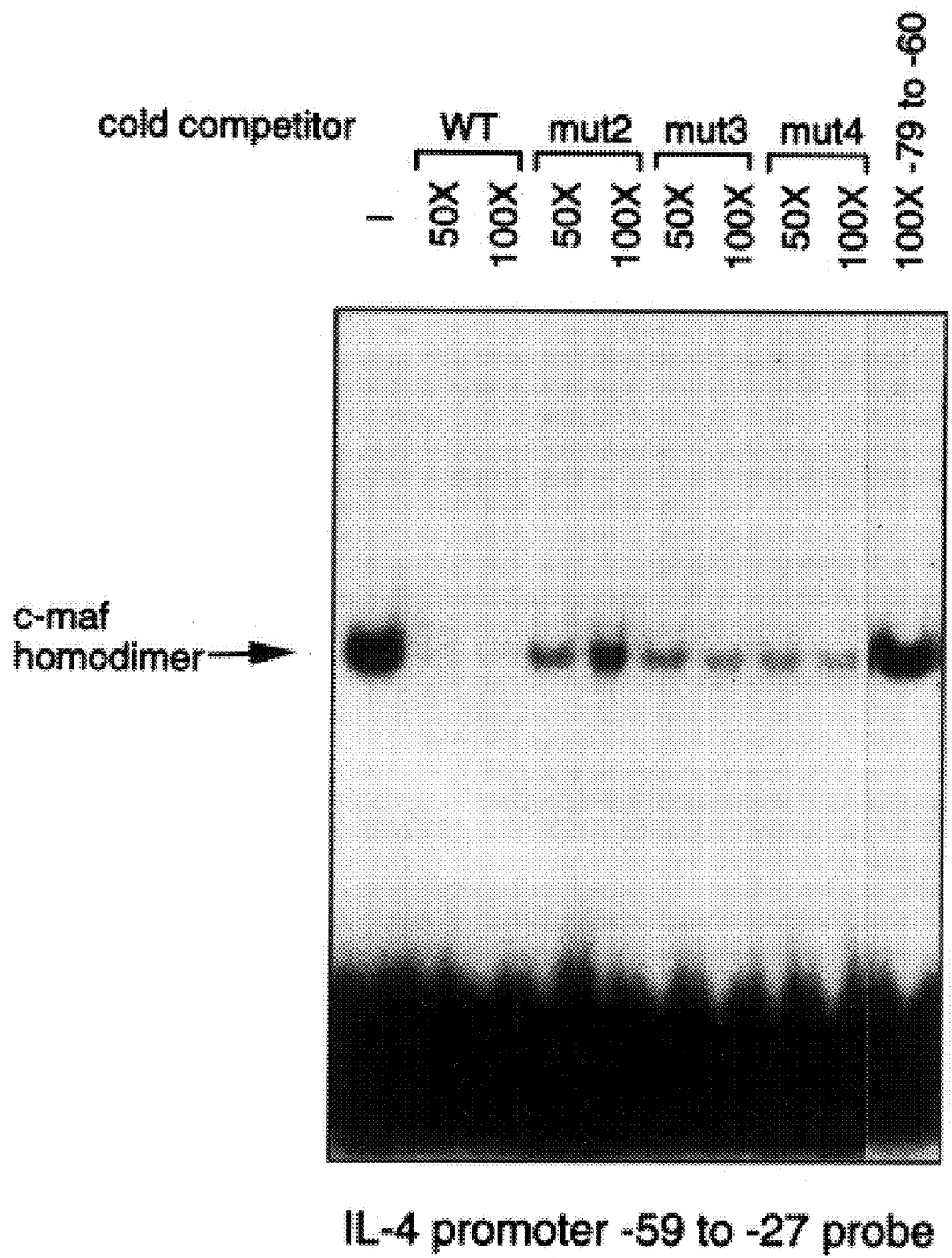
FIG. 7B is a photograph of an EMSA, performed using recombinant c-Maf, the IL-4 promoter (−59 to −27) probe and the indicated unlabeled double-stranded oligonucleotides as competitors, demonstrating that binding of recombinant c-Maf to the IL-4 promoter maps to the MARE and Th2-specific footprint.

The Ability of c-Maf to Transactivate the IL-4 Promoter Maps to the MARE and Th-2 Specific Footprint An essential region of the IL-4 promoter located immediately upstream of the TATA element has been characterized by high resolution mutagenesis (Hodge, M. et al. (1995) *J. Immunol.* 154:6397–6405). Mutagenesis of this 33 bp region (–59 to –28) demonstrated multiple sites required for inducible IL-4 transcription in Th2 cells. These sites included an NF-AT target sequence, the region footprinted by Th2 extracts, and what is now recognized as a MARE. A series of IL-4 reporter gene constructs comprising 4 base pair linker-scanning mutants generated across this region were used to map the target sequence utilized by c-Maf in vivo in M12 cells. These cells were cotransfected with the c-maf expression vector and this series of mutant IL-4 promoter constructs. The results are shown in FIG. 7A. Mutation of the MARE (muts 3 and 4), or the site defined by the Th2 footprint (mut 2), abrogated (muts 2 and 4) or partially abrogated (mut 3) the ability of transfected c-maf to drive IL-4 transcription. A modest effect in reducing c-maf transactivation was also observed for mutant 8 which disrupts the NF-AT sequence, consistent with the presence in M12 cells of endogenous NF-ATp and with the synergy between NF-ATp and c-maf demonstrated in the previous examples. Mutants 6 and 7 had no significant effect while mutant 5 had enhanced transactivation ability, consistent with previous observations in Th2 cells (Hodge, M. et al. (1995) *J. Immunol.* 154:6397–6405). The transactivation data is consistent with EMSA performed with recombinant c-Maf protein using as probe an oligonucleotide which contains this 33 bp region, and this same series of mutant oligonucleotides as cold competitors. The results of these EMSA experiments are shown in FIG. 7B. These experiments indicate that c-Maf specifically binds to and transactivates the MARE in the proximal IL-4 promoter and that the adjacent Th2-specific element is intimately involved in both the binding and finction of c-Maf.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for identifying a compound that modulates the activity of a maf family protein, comprising
providing an indicator composition comprising a maf family protein and a target DNA to which said maf family protein binds, said indicator composition being an indicator cell or an acellular preparation and said target DNA being a regulatory sequence of a Th2-associated cytokine gene, wherein said maf family protein is selected from the group consisting of c-Maf, v-maf, mafB, Nrl, mafK, mafF, mafG and p18;
contacting the indicator composition with a test compound; and
determining the effect of the test compound on binding of the maf family protein to the target DNA in the indicator composition to thereby identify a compound that modulates the activity of a maf family protein.

2. The method of claim 1, wherein the maf family protein is c-Maf.

3. The method of claim 1, wherein the indicator composition is an indicator cell and said indicator cell comprises said maf family protein and a reporter gene construct responsive to said maf family protein, said reporter gene construct comprising the target DNA.

4. The method of claim 3, wherein the indicator cell is a lymphoid cell.

5. The method of claim 4, wherein the lymphoid cell is a Th2 cell.

6. The method of claim 3, wherein the indicator cell is a yeast cell.

7. The method of claim 3, wherein the maf family protein is selected from the group consisting of v-maf, mafB, Nrl, mafK, mafF, mafG and p18.

8. The method of claim 3, wherein the Th2-associated cytokine gene is an interleukin-4 gene.

9. The method of claim 4, wherein the lymphoid cell is a B cell.

10. The method of claim 4, wherein the lymphoid cell is a Th1 cell.

11. The method of claim 3, wherein the indicator cell is a non-lymphoid mammalian cell.

12. The method of claim 1, which identifies a compound that modulates the interaction of said maf family protein with a maf response element (MARE) of an IL-4 gene regulatory region, wherein:
the indicator composition comprises said maf family protein and a DNA fragment comprising a maf response element (MARE) of an IL-4 gene regulatory region;
the method comprising:
a) incubating said maf family protein and the DNA fragment in the presence of a test compound;
b) determining the amount of binding of said maf family protein to the DNA fragment in the presence of the test compound; and
c) comparing the amount of binding of said maf family protein to the DNA fragment in the presence of the test compound with the amount of binding of said maf family protein to the DNA fragment in the absence of the test compound to thereby identify a compound that modulates the interaction of said maf family protein with a MARE of an IL-4 gene regulatory region.

13. The method of claim 12, wherein said maf family protein is c-Maf.

14. A method for identifying a compound that modulates the activity of a maf family protein, comprising:
a) providing an indicator cell comprising:
  i) a recombinant expression vector encoding a maf family protein, said maf family protein being selected from the group consisting of c-Maf, v-maf, mafB, Nrl, mafK, mafF, mafG and p18; and
  ii) a vector comprising regulatory sequences of a Th2-associated cytokine gene operatively linked to a reporter gene;
b) contacting the indicator cell with a test compound;
c) determining the level of expression of the reporter gene in the indicator cell in the presence of the test compound; and
d) comparing the level of expression of the reporter gene in the indicator cell in the presence of the test compound with the level of expression of the reporter gene in the indicator cell in the absence of the test compound to thereby identify a compound that modulates the activity of said maf family protein.

15. The method of claim 14, wherein the Th2-associated cytokine gene is an interleukin-4 gene.

16. The method of claim 14, wherein the indicator cell is a lymphoid cell.

17. The method of claim 14, wherein the indicator cell is a yeast cell.

18. The method of claim 14, wherein the maf family protein is selected from the group consisting of v-maf, mafB, Nrl, mafK, mafF, mafG and p18.

19. The method of claim 16, wherein the lymphoid cell is a B cell.

20. The method of claim 16, wherein the lymphoid cell is a Th1 cell.

21. The method of claim 14, wherein the indicator cell is a non-lymphoid mammalian cell.

22. The method of claim 14, wherein said maf family protein is c-Maf.

23. A method for identifying a protein from Th2 cells that interacts with a maf family protein, comprising:
  a) providing an indicator cell, which indicator cell comprises:
    i) a reporter gene operably linked to a transcriptional regulatory sequence;
    ii) a first chimeric gene which encodes a first fusion protein, said first fusion protein comprising a maf family protein fused to a DNA binding domain or a transcriptional activation domain, wherein said maf family protein is selected from the grouip consisting of c-Maf, v-maf, mafB, Nrl, mafK, mafF, mafG and p18; and
    iii) a second chimeric gene, which encodes a second fusion protein, the second fusion protein comprising a polypeptide encoded by mRNA from a Th2 cell fused to a DNA binding domain or a transcriptional activation domain;
  wherein the first fusion protein comprises a DNA binding domain or transcriptional activation domain when the second fusion protein comprises a transcriptional activation domain or DNA binding domain, respectively and;
  wherein expression of the reporter gene is sensitive to interactions between the first fusion protein, the second fusion protein and the transcriptional regulatory sequence; and
  b) determining the effect of the second fusion protein on maf family protein activity in the indicator cell by determining the level of expression of the reporter gene in the indicator cell to thereby identify a protein from Th2 cells that interacts with said maf family protein.

24. The method of claim 23, wherein the maf family protein is c-Maf.

25. The method of claim 23, wherein the indicator cell is a yeast cell.

26. The method of claim 23, wherein the maf family protein is selected from the group consisting of v-maf, mafB, Nrl, mafK, mafF, mafG and p18.

27. The method of claim 23, wherein a population of indicator cells is provided, said population of indicator cells comprising a library of second chimeric genes made from a Th2 cell cDNA library.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:1:

CTCATTTTCC CTTGGTTTCA GCAACTTTAA CTC                          33

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:2:

ATAAAATTTT CCAATGTAAA                                         20

(2) INFORMATION FOR SEQ ID NO:3:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:3:

TGGTGTAATA AAATTTTCCA ATGTAAA                                 27

(2) INFORMATION FOR SEQ ID NO:4:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:4:

GGAATTGCTG ACTCAGCATT ACT                                     23

(2) INFORMATION FOR SEQ ID NO:5:

(i) SEQUENCE CHARACTERISTICS:
       (A) LENGTH: 83 base pairs
       (B) TYPE: nucleic acid
       (C) STRANDEDNESS: double
       (D) TOPOLOGY: linear (ii) MOLECULE TYPE: DNA (xi) SEQUENCE DESCRIPTION: SEQ ID NO:5:

```
GAATAACTGA CAATCTGGTG TAATAAAATT TTCCAATGTA AACTCATTTT CCCTTGGTTT      60

CAGCAACTTT AACTCTATAT ATA                                             83
```

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

```
CTCATTTTCC CTTGGTTTCA GCAACGGGCA CTC                                   33
```

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:7:

```
CTCATTTTCC CTTGGTTTCA GACCATTTAA CTC                                   33
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:8:

```
CTCATTTTCC CTTGGTTGAC TCAACTTTAA CTC                                   33
```

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

```
CTCATTTTCC CTTTTGGTCA GCAACTTTAA CTC                                   33
```

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

```
CTCATTTTCA AGGGGTTTCA GCAACTTTAA CTC                                   33
```

-continued (2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

CTCATGGGAC CTTGGTTTCA GCAACTTTAA CTC        33

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

CGACGTTTCC CTTGGTTTCA GCAACTTTAA CTC        33